(12) United States Patent
McNeal et al.

(10) Patent No.: US 11,726,351 B2
(45) Date of Patent: Aug. 15, 2023

(54) GOGGLE LENS WITH COMPOUND CURVATURE FOR DOWNWARD FIELD OF VIEW ENHANCEMENT

(71) Applicant: Smith Sport Optics, Inc., Portland, OR (US)

(72) Inventors: Will McNeal, Portland, OR (US); Hans Lindauer, Brooklyn, NY (US); Mike Aaskov, Kennebunkport, ME (US); John Ohran, West Linn, OR (US); Eric Thorsell, Portland, OR (US); Matt Capozzi, Bend, OR (US); Nicolas Ramirez, Portland, OR (US); Scott Layton, Portland, OR (US)

(73) Assignee: Smith Sport Optics, Inc., Portland, OR (US)

( * ) Notice: Subject to any disclaimer, the term of this patent is extended or adjusted under 35 U.S.C. 154(b) by 484 days.

(21) Appl. No.: 16/672,358

(22) Filed: Nov. 1, 2019

(65) Prior Publication Data
US 2020/0142218 A1     May 7, 2020

Related U.S. Application Data

(60) Provisional application No. 62/756,034, filed on Nov. 5, 2018.

(51) Int. Cl.
  *G02C 7/06* (2006.01)
  *A61F 9/02* (2006.01)

(52) U.S. Cl.
  CPC .............. *G02C 7/066* (2013.01); *A61F 9/025* (2013.01); *A61F 9/027* (2013.01); *A61F 9/029* (2013.01); *G02C 7/065* (2013.01)

(58) Field of Classification Search
  CPC .. A61F 9/02; A61F 9/025; A61F 9/026; A61F 9/027; A61F 9/028; A61F 9/029; G02C 7/065; G02C 7/066
  See application file for complete search history.

(56) References Cited

U.S. PATENT DOCUMENTS

| 2,508,870 A | 5/1950 | Splaine |
| 3,484,156 A | 12/1969 | Militello |

(Continued)

FOREIGN PATENT DOCUMENTS

| CA | 2539125 A1 | 4/2005 |
| CA | 2466402 C | 12/2007 |

(Continued)

OTHER PUBLICATIONS

Extended European Search Report for Application No. 19206253.7, dated Mar. 11, 2020.

(Continued)

*Primary Examiner* — F Griffin Hall
(74) *Attorney, Agent, or Firm* — Dorsey & Whitney LLP

(57) ABSTRACT

A goggle may include a goggle frame and a lens assembly that may be removably coupled by magnetic materials and a latch mechanism. The latch mechanism may couple the goggle frame to the lens assembly by mechanically engaging latch components. The latch mechanism may couple the goggle frame to the lens assembly by magnetically coupling latch components. Latch components may be included with the lens assembly and the goggle frame. The goggle frame may include an elastomer face gasket. The goggle frame may include outriggers fixedly coupled to the face gasket. The lens assembly may include an elastomer lens frame.

30 Claims, 28 Drawing Sheets

(56) References Cited

U.S. PATENT DOCUMENTS

| | | | |
|---|---|---|---|
| 3,691,565 A * | 9/1972 | Galonek | A61F 9/02 2/431 |
| D228,584 S | 10/1973 | LeBlanc | |
| 4,026,640 A | 5/1977 | Everburg | |
| 4,240,718 A * | 12/1980 | Wichers | G02C 11/08 351/83 |
| 4,699,479 A | 10/1987 | Metcalfe | |
| 4,730,915 A | 3/1988 | Jannard | |
| 4,878,749 A | 11/1989 | Mcgee | |
| 4,964,714 A * | 10/1990 | Weymouth, Jr. | A61F 9/025 351/111 |
| 4,968,129 A | 11/1990 | Grendol | |
| 4,998,815 A | 3/1991 | Lin | |
| 5,013,145 A | 5/1991 | Croll | |
| 5,110,199 A | 5/1992 | Ishida | |
| 5,170,190 A | 12/1992 | Berke | |
| 5,432,568 A | 7/1995 | Betz et al. | |
| 5,452,029 A | 9/1995 | Yang | |
| 5,457,502 A * | 10/1995 | Iida | A61F 9/02 351/44 |
| 5,489,953 A | 2/1996 | Griffith | |
| 5,532,767 A | 7/1996 | Pleune et al. | |
| D377,036 S | 12/1996 | Leonardi | |
| 5,594,511 A | 1/1997 | Lin | |
| 5,614,964 A | 3/1997 | Garneau | |
| 5,617,588 A * | 4/1997 | Canavan | A44B 11/04 2/431 |
| 5,703,669 A | 12/1997 | Park | |
| 5,774,201 A | 6/1998 | Tackles | |
| 5,841,505 A * | 11/1998 | Bolle' | G02C 7/02 351/44 |
| 5,867,841 A * | 2/1999 | Chiang | A61F 9/02 2/439 |
| D419,166 S | 1/2000 | Wiedner | |
| 6,009,564 A * | 1/2000 | Tackles | G02C 7/02 351/158 |
| 6,010,218 A * | 1/2000 | Houston | A61F 9/02 351/41 |
| 6,036,315 A * | 3/2000 | Copeland | G02C 7/02 351/44 |
| 6,038,705 A | 3/2000 | Jarvis | |
| 6,053,611 A | 4/2000 | Ku | |
| D424,080 S | 5/2000 | Hall et al. | |
| D428,039 S | 7/2000 | Thixton | |
| 6,098,207 A | 8/2000 | Burtin | |
| 6,105,177 A * | 8/2000 | Paulson | A61F 9/029 2/431 |
| 6,120,144 A | 9/2000 | Park | |
| 6,129,435 A * | 10/2000 | Reichow | A61F 9/02 351/178 |
| 6,139,142 A | 10/2000 | Zelman | |
| 6,149,269 A | 11/2000 | Madison | |
| 6,176,576 B1 * | 1/2001 | Green | G02C 11/10 351/158 |
| 6,196,676 B1 * | 3/2001 | Tabacchi | A61F 9/029 351/41 |
| 6,253,388 B1 | 7/2001 | Lando | |
| 6,254,236 B1 * | 7/2001 | Fecteau | G02C 7/02 351/41 |
| 6,264,327 B1 | 7/2001 | Copeland | |
| 6,361,166 B1 | 3/2002 | Perrott et al. | |
| 6,402,318 B1 | 6/2002 | Xiao | |
| RE37,816 E | 8/2002 | Kranhouse | |
| 6,446,272 B1 | 9/2002 | Lee | |
| 6,505,932 B2 | 1/2003 | Xiao | |
| 6,540,352 B2 * | 4/2003 | Billard | G02C 7/02 351/159.68 |
| D477,010 S | 7/2003 | Mortiz et al. | |
| 6,585,370 B2 | 7/2003 | Zelman | |
| 6,592,220 B1 | 7/2003 | Cheong | |
| 6,601,953 B1 | 8/2003 | Xiao | |
| 6,623,116 B2 | 9/2003 | Kerns, Jr. et al. | |
| 6,695,448 B2 | 2/2004 | Xiao | |
| 6,755,522 B1 | 6/2004 | Strenk | |
| 6,755,525 B2 | 6/2004 | Reichow et al. | |
| 6,764,175 B1 | 7/2004 | Chen | |
| 6,789,896 B2 | 9/2004 | Morris et al. | |
| 6,866,385 B2 | 3/2005 | Madison et al. | |
| 6,871,952 B2 | 3/2005 | Pierotti | |
| 6,893,126 B2 | 5/2005 | Iori et al. | |
| 6,926,402 B1 | 8/2005 | Chen et al. | |
| 6,942,337 B2 | 9/2005 | Zelman | |
| 6,964,067 B1 | 11/2005 | Hartman | |
| 6,991,333 B2 | 1/2006 | Van et al. | |
| D515,615 S | 2/2006 | Fecteau et al. | |
| 7,029,114 B2 | 4/2006 | Smith | |
| 7,036,926 B2 | 5/2006 | Xiao | |
| 7,040,749 B2 | 5/2006 | Smith | |
| 7,040,751 B2 | 5/2006 | Madison | |
| 7,070,274 B2 | 7/2006 | Kamishita et al. | |
| 7,073,208 B2 * | 7/2006 | Penque, Jr. | A61F 9/028 2/431 |
| 7,097,299 B2 | 8/2006 | Zelman | |
| 7,134,752 B2 | 11/2006 | Perrott et al. | |
| 7,207,673 B1 | 4/2007 | Ho | |
| 7,237,891 B2 | 7/2007 | Min | |
| 7,241,007 B2 | 7/2007 | Cody | |
| D548,251 S | 8/2007 | Broersma | |
| 7,305,719 B2 * | 12/2007 | Pan | A63B 33/004 2/430 |
| 7,338,160 B2 | 3/2008 | Lieberman et al. | |
| 7,347,545 B1 | 3/2008 | Jannard et al. | |
| 7,370,961 B2 | 5/2008 | Lerner et al. | |
| 7,403,346 B2 | 7/2008 | Reichow et al. | |
| 7,431,453 B2 | 10/2008 | Hogan | |
| 7,448,750 B2 | 11/2008 | Tackles | |
| 7,497,569 B2 | 3/2009 | Webb | |
| 7,520,605 B1 | 4/2009 | Chen | |
| 7,527,376 B2 | 5/2009 | Kamishita et al. | |
| 7,537,336 B2 | 5/2009 | Zelman | |
| 7,568,797 B2 | 8/2009 | Hibbs, Jr. | |
| 7,594,723 B2 | 9/2009 | Jannard et al. | |
| D606,112 S | 12/2009 | Markovitz | |
| 7,661,815 B2 | 2/2010 | Lipawsky | |
| 7,744,213 B2 | 6/2010 | Jannard et al. | |
| 7,771,044 B2 | 8/2010 | Madison | |
| 7,784,937 B2 | 8/2010 | Keane et al. | |
| D629,034 S | 12/2010 | McNeal et al. | |
| 7,874,673 B2 | 1/2011 | Shinohara et al. | |
| 7,896,493 B2 | 3/2011 | Welk et al. | |
| D640,724 S | 6/2011 | Goodman et al. | |
| 7,967,431 B2 | 6/2011 | Siu | |
| 7,971,995 B2 | 7/2011 | Wade et al. | |
| 7,976,158 B2 | 7/2011 | Drobe | |
| 8,025,396 B1 | 9/2011 | Power | |
| D649,577 S | 11/2011 | Goodman et al. | |
| 8,061,836 B2 * | 11/2011 | Tabacchi | B29D 11/00009 351/110 |
| 8,092,007 B2 | 1/2012 | DiChiara | |
| 8,104,891 B2 | 1/2012 | Reichow et al. | |
| D653,686 S | 2/2012 | Tobia | |
| D653,695 S | 2/2012 | Tobia | |
| D657,812 S | 4/2012 | Li | |
| 8,192,019 B2 | 6/2012 | Hsu | |
| D670,753 S | 11/2012 | Chen | |
| 8,469,510 B2 | 6/2013 | Beleby et al. | |
| 8,480,226 B2 | 7/2013 | Ifergan | |
| 8,534,830 B2 | 9/2013 | Wade et al. | |
| 8,555,425 B2 | 10/2013 | Keegan | |
| D695,335 S | 12/2013 | Goodman et al. | |
| D695,818 S | 12/2013 | Laperriere et al. | |
| 8,641,188 B2 | 2/2014 | DiChiara | |
| 8,661,562 B2 | 3/2014 | Calilung et al. | |
| 8,668,330 B2 | 3/2014 | Reyes et al. | |
| 8,746,877 B2 | 6/2014 | Belbey et al. | |
| D711,960 S | 8/2014 | Mage et al. | |
| D711,961 S | 8/2014 | Arnette | |
| 8,800,067 B2 | 8/2014 | Saylor et al. | |
| D714,378 S | 9/2014 | Sandor | |
| 8,832,904 B2 | 9/2014 | Kidouchim | |
| D715,350 S | 10/2014 | Moritz et al. | |
| D718,369 S | 11/2014 | Janavicius et al. | |

(56) References Cited

U.S. PATENT DOCUMENTS

| | | | |
|---|---|---|---|
| 8,917,459 B2 | 12/2014 | Klein et al. | |
| D723,094 S | 2/2015 | Chen | |
| D725,690 S | 3/2015 | Garfias | |
| 9,010,928 B2 | 4/2015 | Fuchs et al. | |
| D729,303 S | 5/2015 | Laperriere et al. | |
| D730,430 S | 5/2015 | Tanguy et al. | |
| 9,104,043 B2 | 8/2015 | Crescenzi et al. | |
| 9,122,078 B2 | 9/2015 | Calilung et al. | |
| D741,323 S | 10/2015 | Bosveld et al. | |
| D741,858 S * | 10/2015 | Bosveld | D14/372 |
| 9,170,432 B2 | 10/2015 | Spratt et al. | |
| 9,176,329 B2 | 11/2015 | Kelch | |
| 9,192,519 B2 * | 11/2015 | Tobia | G02C 9/00 |
| 9,220,633 B2 | 12/2015 | Tobia | |
| 9,241,527 B2 * | 1/2016 | Croteau | F41H 1/04 |
| 9,241,833 B2 | 1/2016 | Cater et al. | |
| 9,310,521 B2 | 4/2016 | Meschenmoser et al. | |
| 9,341,865 B2 | 5/2016 | Sheldon et al. | |
| 9,364,718 B1 * | 6/2016 | Tracy | A63B 33/004 |
| D769,350 S | 10/2016 | Orzeck et al. | |
| 9,459,468 B2 | 10/2016 | Wietschorke | |
| 9,463,117 B2 | 10/2016 | Belbey et al. | |
| D774,123 S | 12/2016 | Chae | |
| D776,187 S | 1/2017 | Tappeiner et al. | |
| D777,826 S | 1/2017 | Shin | |
| 9,585,791 B2 | 3/2017 | Isabelle | |
| D783,697 S | 4/2017 | Chae | |
| D785,699 S | 5/2017 | Chen | |
| 9,645,414 B2 | 5/2017 | Perricone et al. | |
| 9,795,513 B2 | 10/2017 | Padovani | |
| D805,576 S | 12/2017 | Garfias | |
| D811,664 S | 2/2018 | Knauer et al. | |
| 9,895,266 B2 | 2/2018 | Reynolds et al. | |
| 9,943,444 B2 | 4/2018 | Kilduff et al. | |
| D818,031 S | 5/2018 | Garfias | |
| 9,956,117 B2 | 5/2018 | Didier | |
| D821,037 S | 6/2018 | Wallis | |
| D827,007 S | 8/2018 | Garfias | |
| D827,208 S | 8/2018 | Baudet | |
| D827,690 S | 9/2018 | Shin | |
| D828,866 S | 9/2018 | Yoo et al. | |
| D829,810 S | 10/2018 | Nellestam | |
| 10,111,780 B2 | 10/2018 | O'malley | |
| D834,087 S | 11/2018 | Yoo et al. | |
| D847,248 S | 4/2019 | Liang | |
| 10,357,400 B2 | 7/2019 | Ginther et al. | |
| D864,285 S * | 10/2019 | Liang | D16/313 |
| D868,878 S | 12/2019 | Langenwalter et al. | |
| D872,168 S | 1/2020 | Zhang | |
| D872,169 S | 1/2020 | Yong | |
| 10,687,981 B2 * | 6/2020 | Calilung | A61F 9/028 |
| D892,913 S | 8/2020 | Lindauer et al. | |
| 10,948,746 B2 | 3/2021 | Langenwalter et al. | |
| 2002/0101565 A1 * | 8/2002 | Yamaguchi | G02C 7/06 351/159.41 |
| 2003/0142264 A1 | 7/2003 | Westerdal et al. | |
| 2004/0046929 A1 | 3/2004 | Wu | |
| 2004/0141146 A1 | 7/2004 | Blanchette et al. | |
| 2005/0206841 A1 | 9/2005 | Saderholm et al. | |
| 2006/0005299 A1 | 1/2006 | Lerner | |
| 2007/0058130 A1 | 3/2007 | Babineau et al. | |
| 2007/0153230 A1 | 7/2007 | Musal et al. | |
| 2007/0261155 A1 | 11/2007 | Tabacchi | |
| 2008/0189838 A1 | 8/2008 | Mage | |
| 2008/0304005 A1 | 12/2008 | Dichiara | |
| 2009/0038059 A1 | 2/2009 | McNeal et al. | |
| 2011/0051074 A1 | 3/2011 | Arnell | |
| 2011/0187985 A1 | 8/2011 | Lin | |
| 2011/0199680 A1 | 8/2011 | Saylor et al. | |
| 2011/0273661 A1 | 11/2011 | Lin | |
| 2012/0038878 A1 | 2/2012 | Echevarria | |
| 2012/0255104 A1 | 10/2012 | Didier | |
| 2013/0077042 A1 | 3/2013 | Calilung et al. | |
| 2013/0104300 A1 | 5/2013 | Park | |
| 2013/0185849 A1 | 7/2013 | Laughlin et al. | |
| 2014/0157496 A1 | 6/2014 | Ginther et al. | |
| 2014/0182754 A1 * | 7/2014 | Young | A45C 11/00 150/154 |
| 2014/0300854 A1 | 10/2014 | Fox | |
| 2015/0121611 A1 | 5/2015 | Isabelle | |
| 2015/0153591 A1 | 6/2015 | Croft et al. | |
| 2015/0202088 A1 | 7/2015 | Sanchez et al. | |
| 2015/0245675 A1 | 9/2015 | Chinquee | |
| 2015/0272783 A1 | 10/2015 | Padovani | |
| 2015/0338680 A1 | 11/2015 | Spratt et al. | |
| 2015/0338683 A1 | 11/2015 | Perricone et al. | |
| 2016/0026004 A1 | 1/2016 | Sheldon et al. | |
| 2016/0106592 A1 | 4/2016 | Tobia | |
| 2016/0287444 A1 | 10/2016 | Han et al. | |
| 2016/0327810 A1 | 11/2016 | Cross | |
| 2016/0331591 A1 | 11/2016 | Kilduff et al. | |
| 2017/0105874 A1 | 4/2017 | Reynolds et al. | |
| 2017/0128267 A1 | 5/2017 | Rees et al. | |
| 2019/0113773 A1 | 4/2019 | Langenwalter et al. | |
| 2019/0142639 A1 * | 5/2019 | Durham | A61F 9/02 2/439 |
| 2021/0077850 A1 | 3/2021 | Baker et al. | |
| 2021/0177688 A1 * | 6/2021 | Ashby | A61H 5/00 |
| 2021/0236338 A1 | 8/2021 | Langenwalter et al. | |

FOREIGN PATENT DOCUMENTS

| | | |
|---|---|---|
| CA | 2849454 C | 8/2016 |
| CN | 1734958 A | 2/2006 |
| CN | 103945805 A | 7/2014 |
| CN | 104114132 A | 10/2014 |
| CN | 206080839 U | 4/2017 |
| CN | 106618852 A | 5/2017 |
| CN | 206261719 U | 6/2017 |
| EP | 0588215 A1 | 3/1994 |
| EP | 1127290 A1 | 8/2001 |
| EP | 0844833 B1 | 5/2003 |
| EP | 1069878 B1 | 6/2006 |
| EP | 1124519 B1 | 2/2007 |
| EP | 1721206 B1 | 3/2011 |
| EP | 2305189 B1 | 5/2013 |
| EP | 3062143 A1 | 8/2016 |
| GB | 2281635 A | 3/1995 |
| WO | 9741481 A1 | 11/1997 |
| WO | 2016011527 A1 | 1/2016 |

OTHER PUBLICATIONS

U.S. Appl. No. 29/669,091 titled "Goggle", filed Nov. 5, 2018.

"Oakley Flight Deck XM Snow Googles", https://www.oakley.com/en-us/product/W0OO7064S?variant=888392104014, site visited Apr. 14, 2020.

"Rimless EVO Goggles", http://www2.carreraworld.com/content/carreraworld_us/en/sport/car/2017/RIMLESS-EVO-US.M004117AS990H.html, site visited Apr. 14, 2020.

"Smith Optics Skyline Snow Goggles", https://www.amazon.com/Smith-Optics-2019-Skyline-Goggles/dp/B07D9DLTJ8?th=1, posted Jan. 8, 2019 online.

"Vonzipper Encore Snow Goggle", https://us.vonzipper.com/shop/product/snow-goggles/encore, site visited Apr. 14, 2020.

* cited by examiner

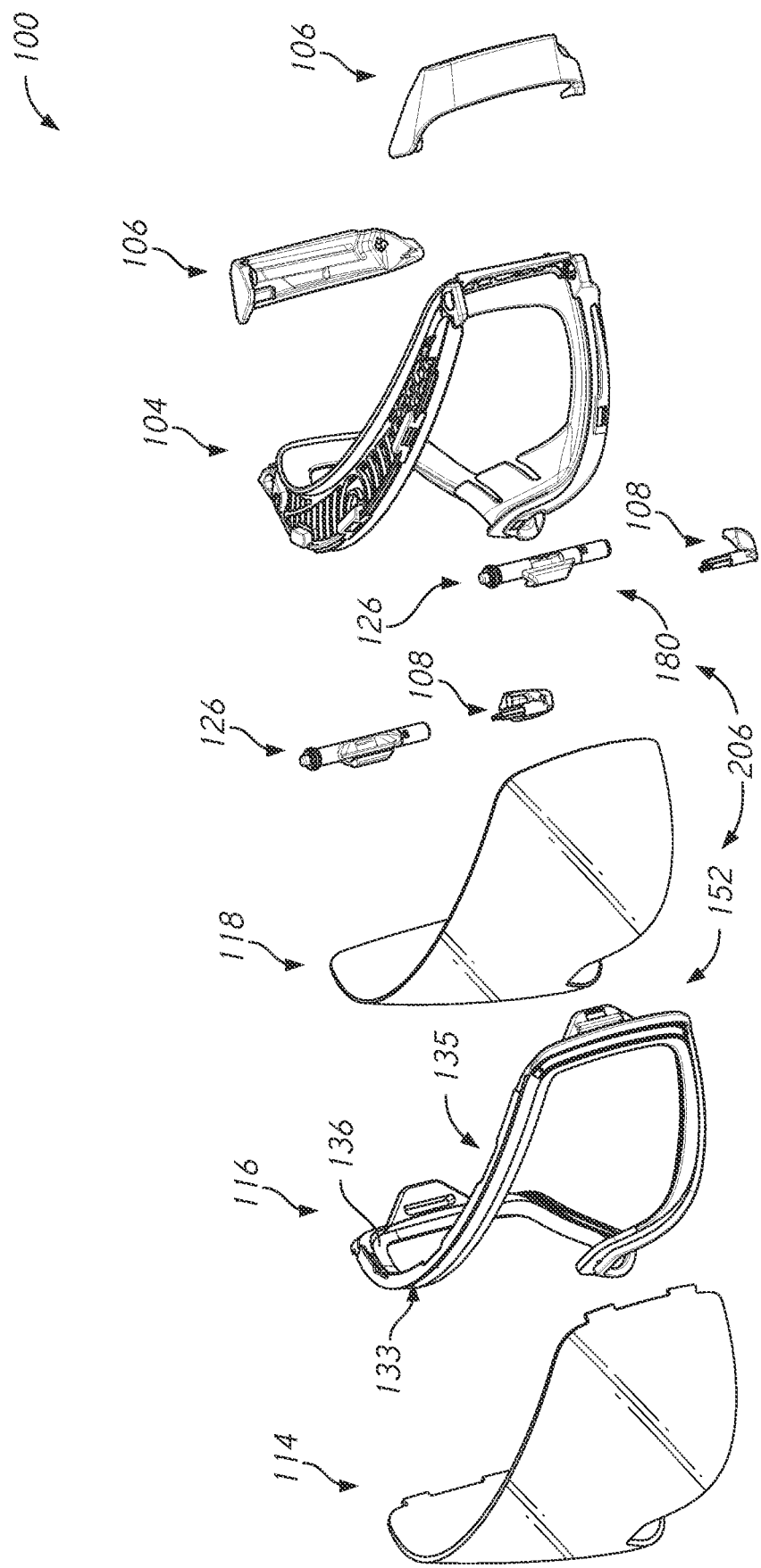

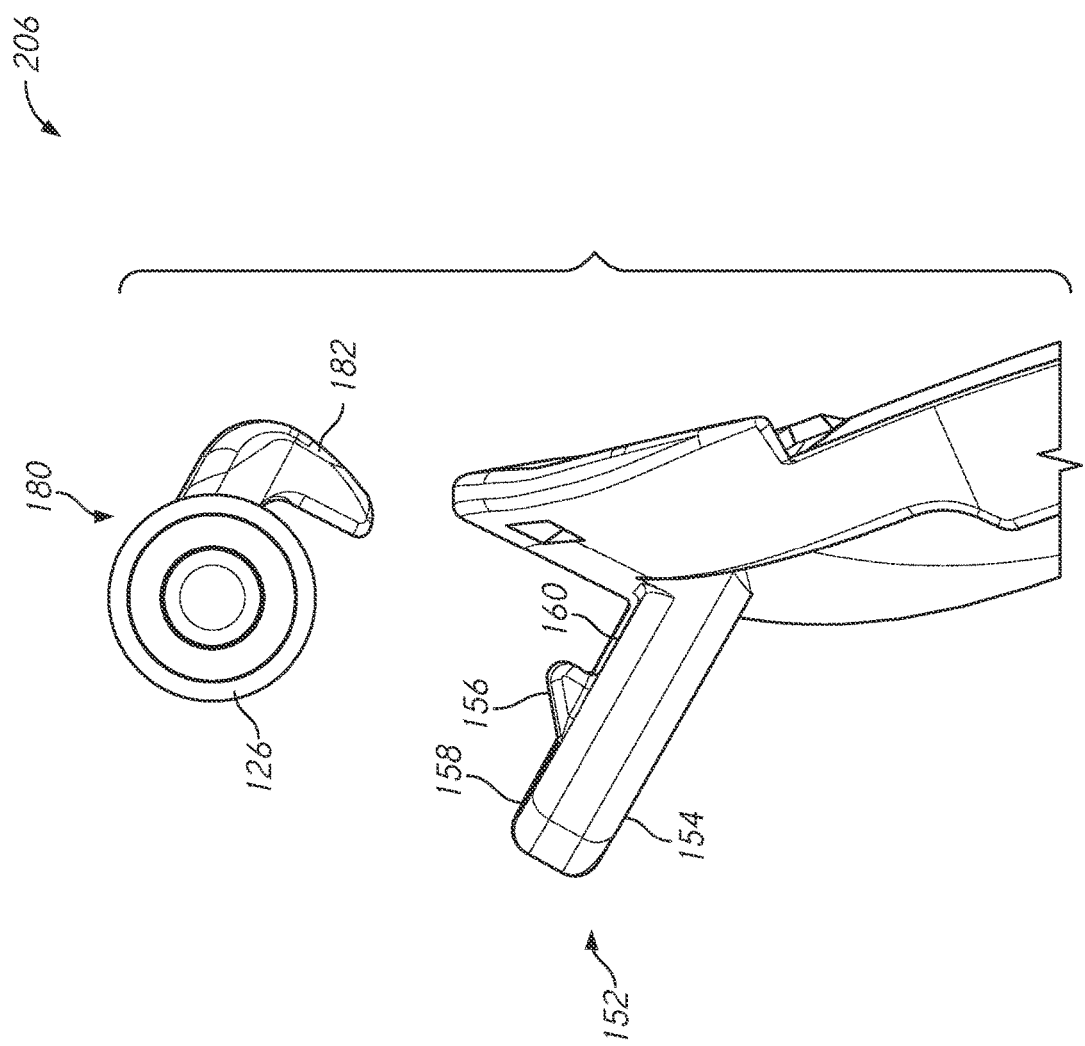

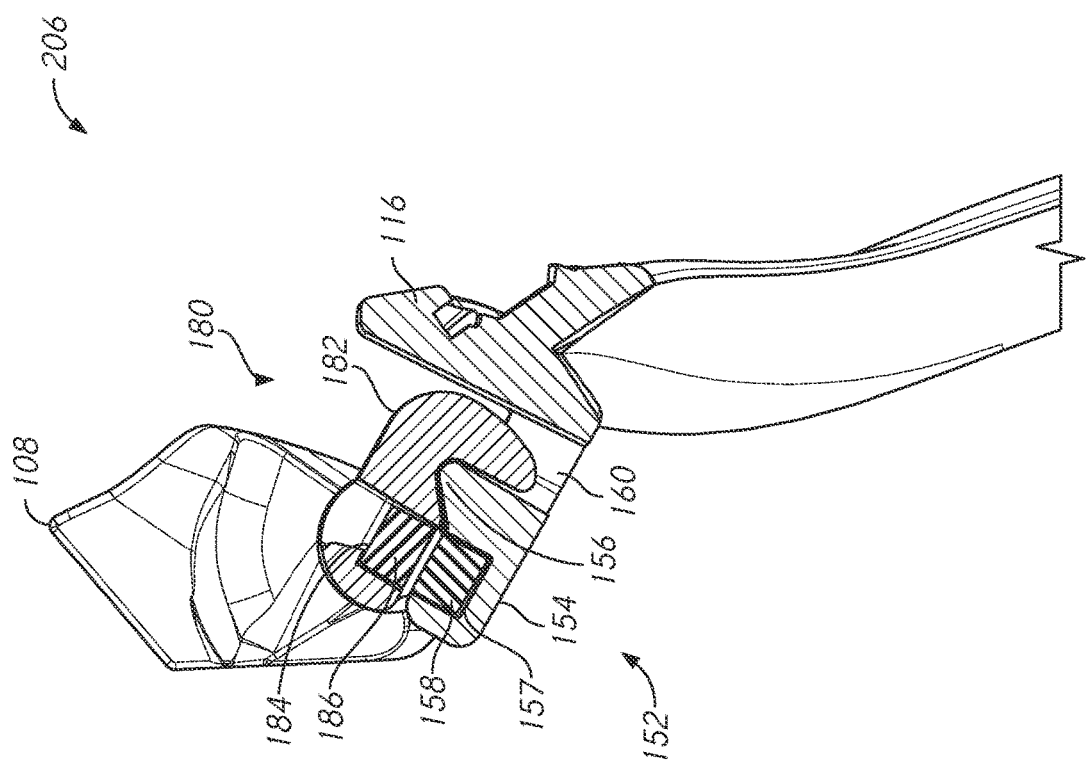

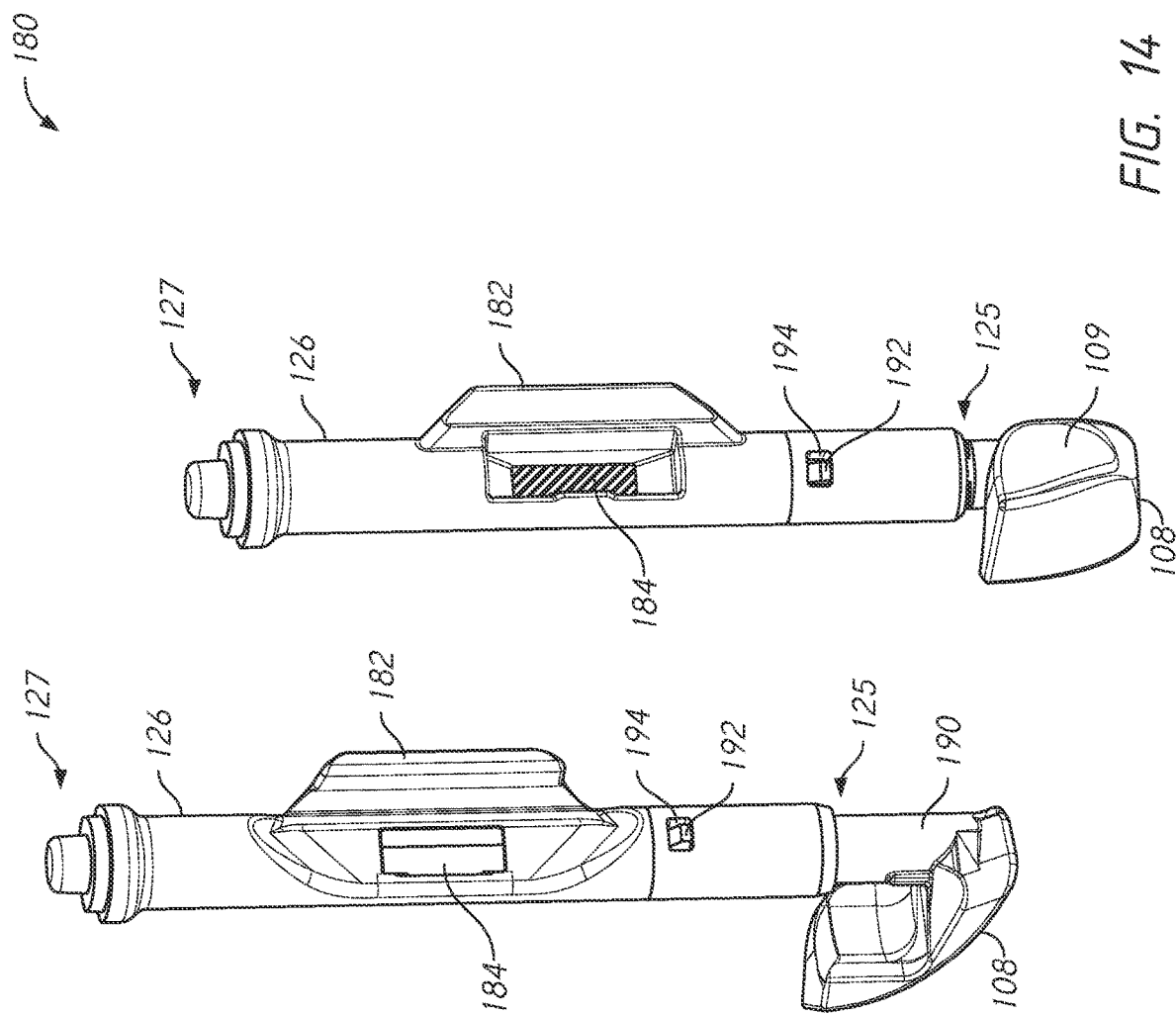

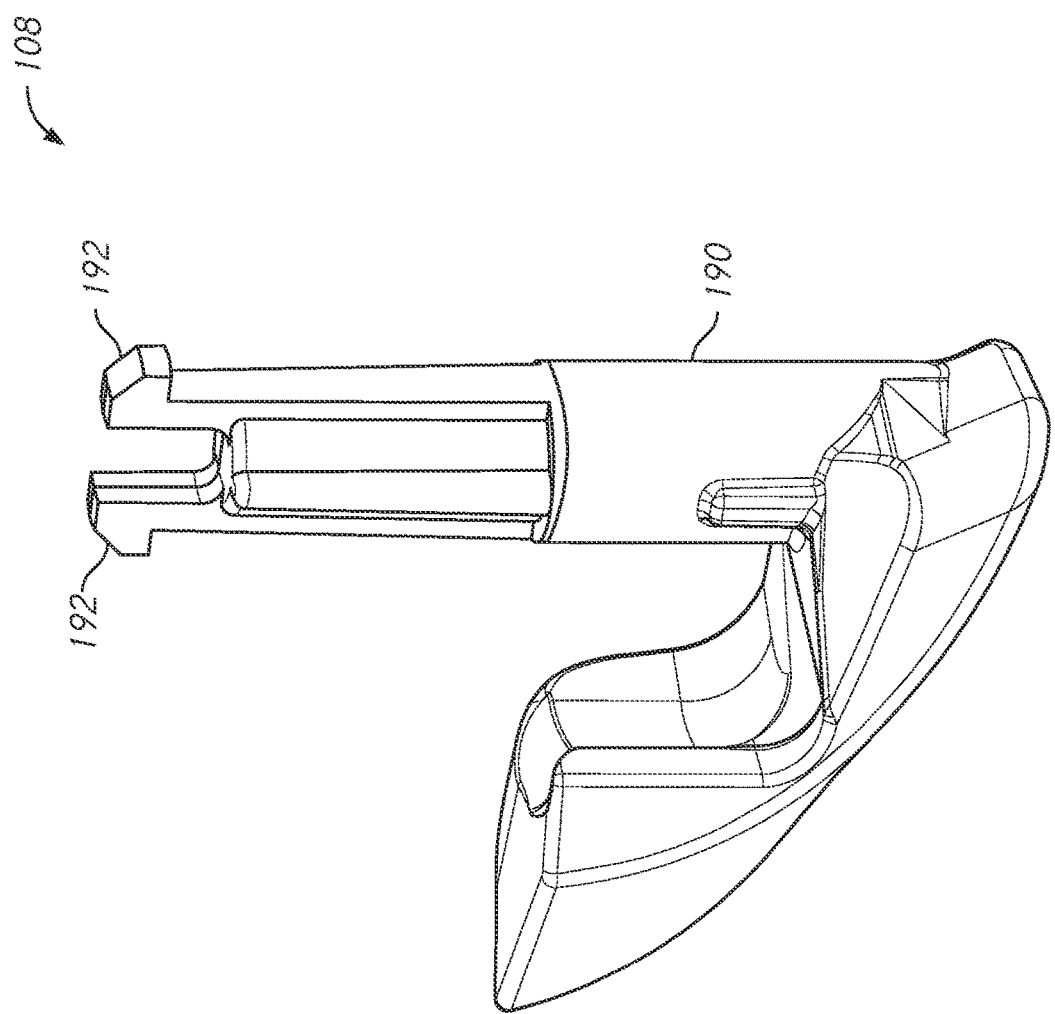

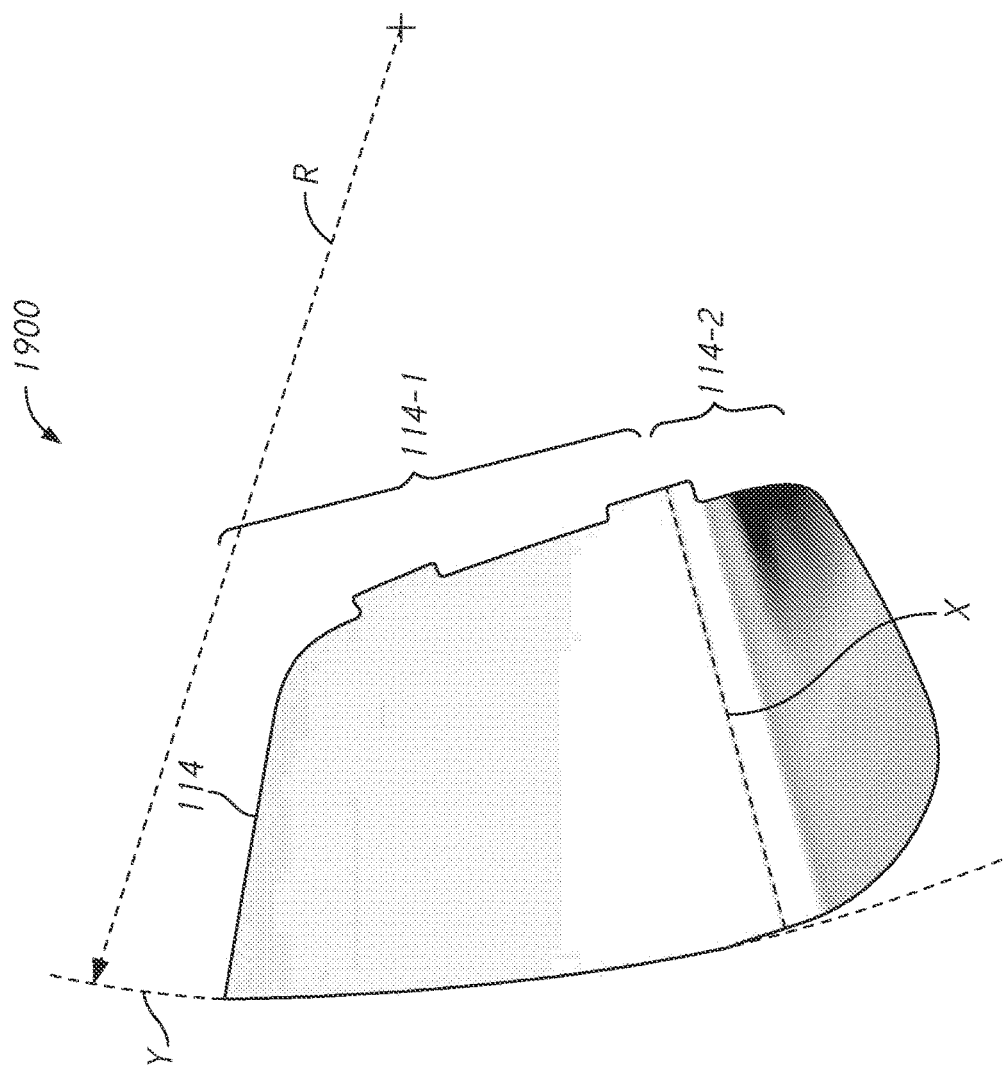
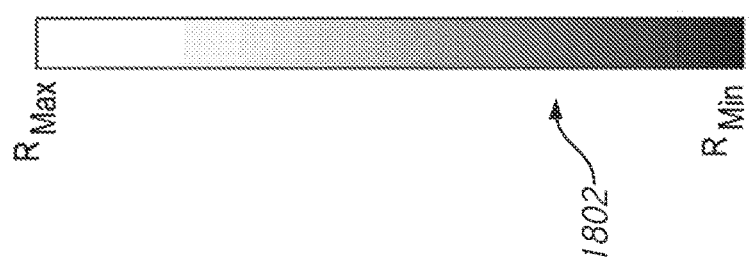
FIG. 19

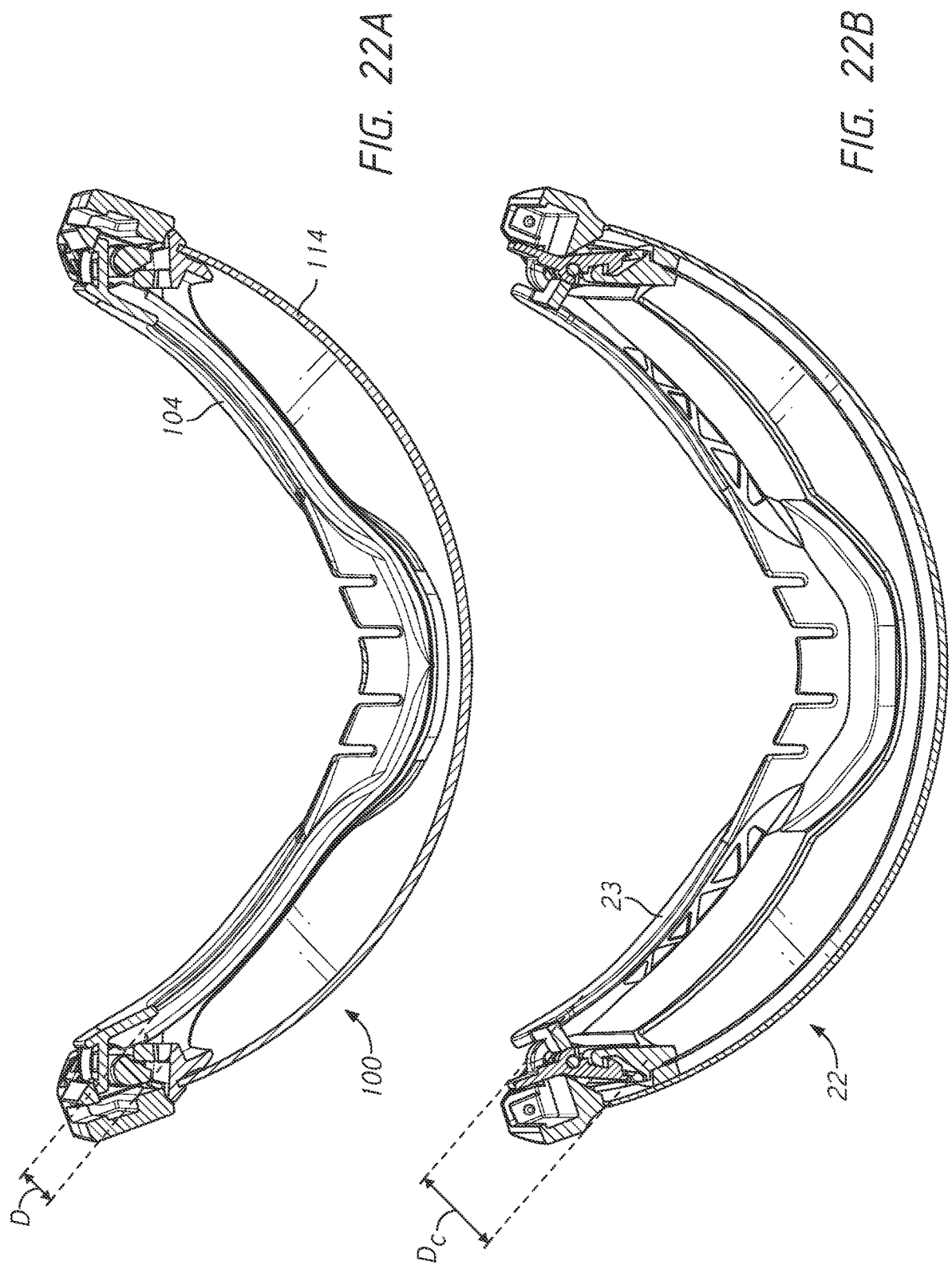

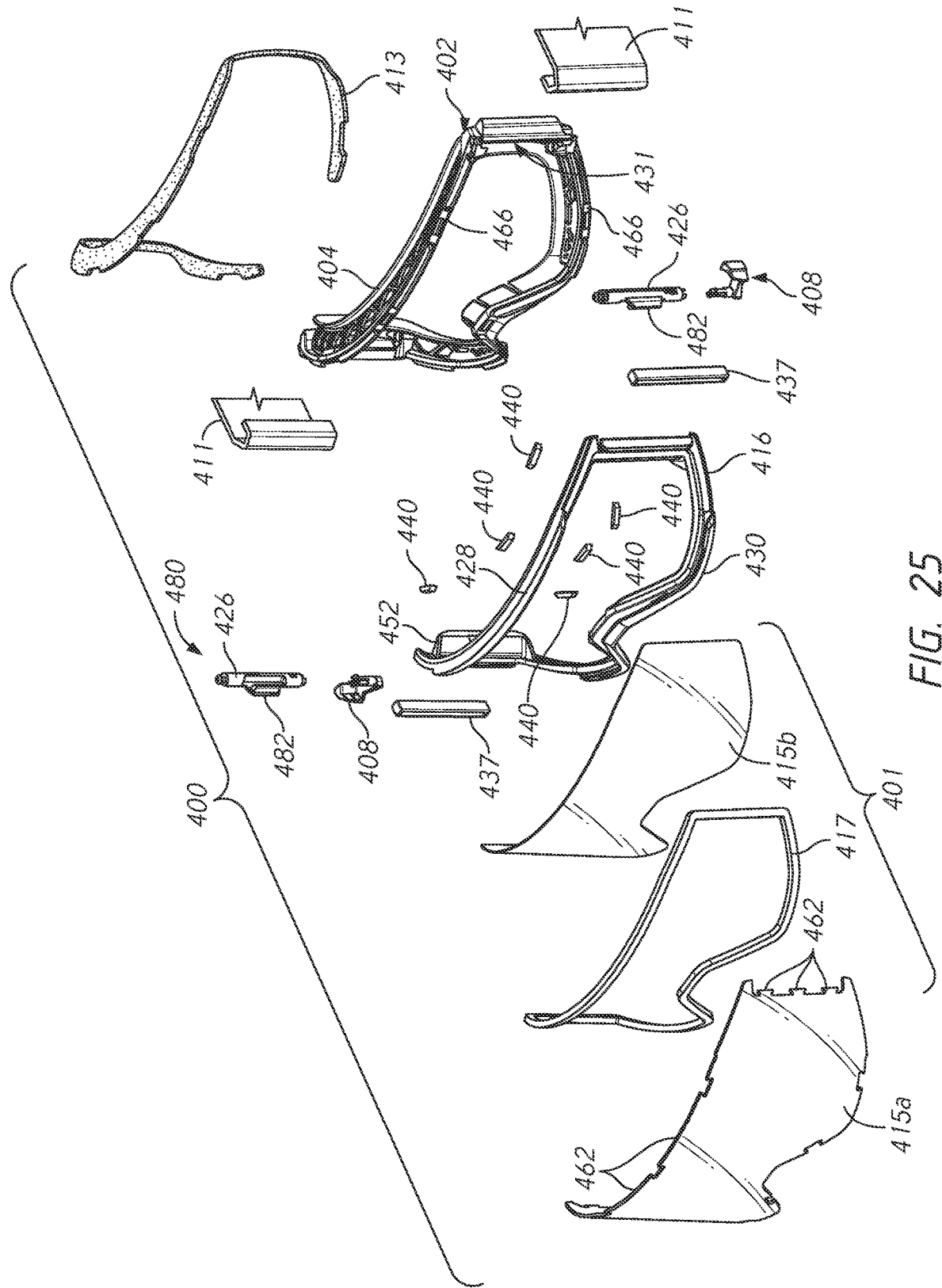

GOGGLE LENS WITH COMPOUND CURVATURE FOR DOWNWARD FIELD OF VIEW ENHANCEMENT

CROSS-REFERENCE TO RELATED APPLICATION(S)

This application claims priority to U.S. Application No. 62/756,034 filed Nov. 5, 2018 which is incorporated herein by reference, in its entirety, for any purpose.

BACKGROUND

Goggles, such as snow or ski goggles, are often used by users to protect their eyes for example when participating in various sports, including snow sports, downhill biking and motocross. Goggles for sporting activities are now frequently designed to have interchangeable lenses such as to allow the user to easily exchange one lens (e.g., a darker tinted lens) for a different lens (e.g., a clear or lighter tinted lens) in order to adapt the same goggle for different use conditions. Goggles with replaceable lenses typically include a frame and one or more removable lenses. The frame may be equipped with a mechanism for attachment of the lens. In some goggles, the lens is attached to the frame with magnets. However, in existing goggles of this kind, the lens may be easily dislodged from the frame. In addition, removal of the lens in existing such goggles may be unduly complex or cumbersome for a user, or may have other deficiencies that may result in a less than ideal user experience.

Newer goggle are designed with the goal of providing a large unobstructed view to the user, which has been largely achieved in existing goggles by the introduction of rimless or substantially rimless frame designs. However shortcomings still remain in the field of goggle design and for these reasons or other reasons, improvements in goggles with removable lenses may be desired.

BRIEF DESCRIPTION OF THE DRAWINGS

The description will be more fully understood with reference to the following figures in which components may not be drawn to scale, which are presented as various embodiments of the eyewear and eyewear components described herein and should not be construed as a complete depiction of the scope of the present disclosure.

FIG. 4 is an exploded view of the goggle in FIG. 1.

FIG. 12 is a partial exploded view of a latch mechanism in accordance with some examples of the present disclosure.

FIG. 13A is a view of a latch mechanism in an engaged position in accordance with some examples of the present disclosure.

FIG. 14 is a view of a latch component in accordance with some examples of the present disclosure.

FIG. 15 is a view of an actuator in accordance with some examples of the present disclosure.

FIG. 19 is a color map of a side view of the lens in accordance with some embodiments of the present disclosure.

FIG. 22A shows a section view of the goggle in FIG. 1 taken along lines 22A-22A in FIG. 2

FIG. 22B shows a similar sectional view as in FIG. 22A but of a conventional goggle.

FIG. 25 shows another exploded view of the goggle in FIG. 24.

DETAILED DESCRIPTION

As used herein, the terms "front" and "forward" are used to refer to edges, surfaces, or other elements of a goggle that are generally distal to a user's face when the goggle is worn by the user. The terms "back" and "rear" are used to refer to edges, surfaces, or other elements of the goggle that are generally proximal to the user's face when the goggle is worn. The terms "top" and "upper" are used to refer to edges, surfaces, or other elements of the goggle that are generally proximal a forehead of the user when the goggle is worn. The terms "bottom" and "lower" are used to refer to edges, surfaces, or other elements of the goggle that are generally proximal a nose, cheek, and/or chin of the user when the goggle is worn. The term "medial" implies locations or elements closer to the midline, or dividing line, between right and left halves of the goggle, and the term "lateral" implies locations or elements that are farther away from the midline.

Examples of goggles with removable lenses are described. In some examples, the goggle may include a first retention feature (e.g., magnetic elements) that couple a lens assembly to a goggle frame. To limit inadvertent decoupling of the lens assembly from the goggle frame, the goggle may include a second retention feature (e.g., a latch mechanism)

for securing the lens assembly to the goggle frame. In some embodiments, the latch mechanism may include a latch component coupled to the goggle frame and a latch component coupled to the lens assembly. In some embodiments, the latch components of the goggle frame and the lens assembly may mechanically engage to secure the lens assembly to the goggle frame. In some embodiments, the latch components of the goggle frame and the lens assembly may magnetically as well as mechanically engage to secure the lens assembly to the goggle frame. In some embodiments, one of the latch components may include a key and the other latch component may include a keyway to engage the key to latch the lens assembly to the goggle frame. In some embodiments, the latch mechanism may include magnetic elements to retain the key in the keyway for latching the lens assembly to the goggle frame. In some embodiments, the latch mechanism may include an actuator configured for manipulation by a user to release and/or engage the latch components. The actuator may be arranged such that it is accessible to the user when the goggle is worn. In some embodiments, the actuator may be included on the goggle frame. In other embodiments, the actuator may be on the lens assembly.

Figure 1:
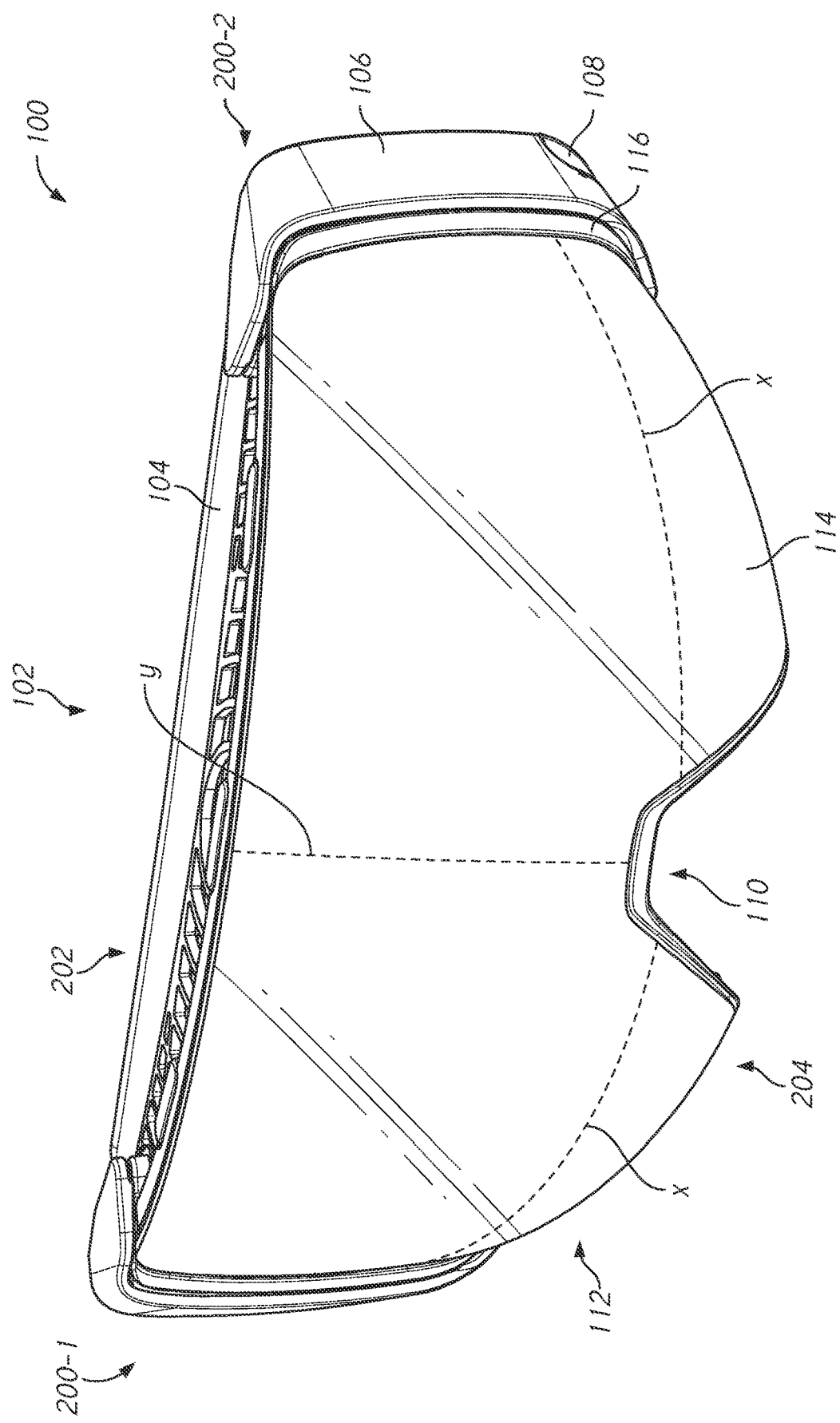
FIG. 1 is an isometric view of a goggle in accordance with some examples of the present disclosure.
Figure 3:
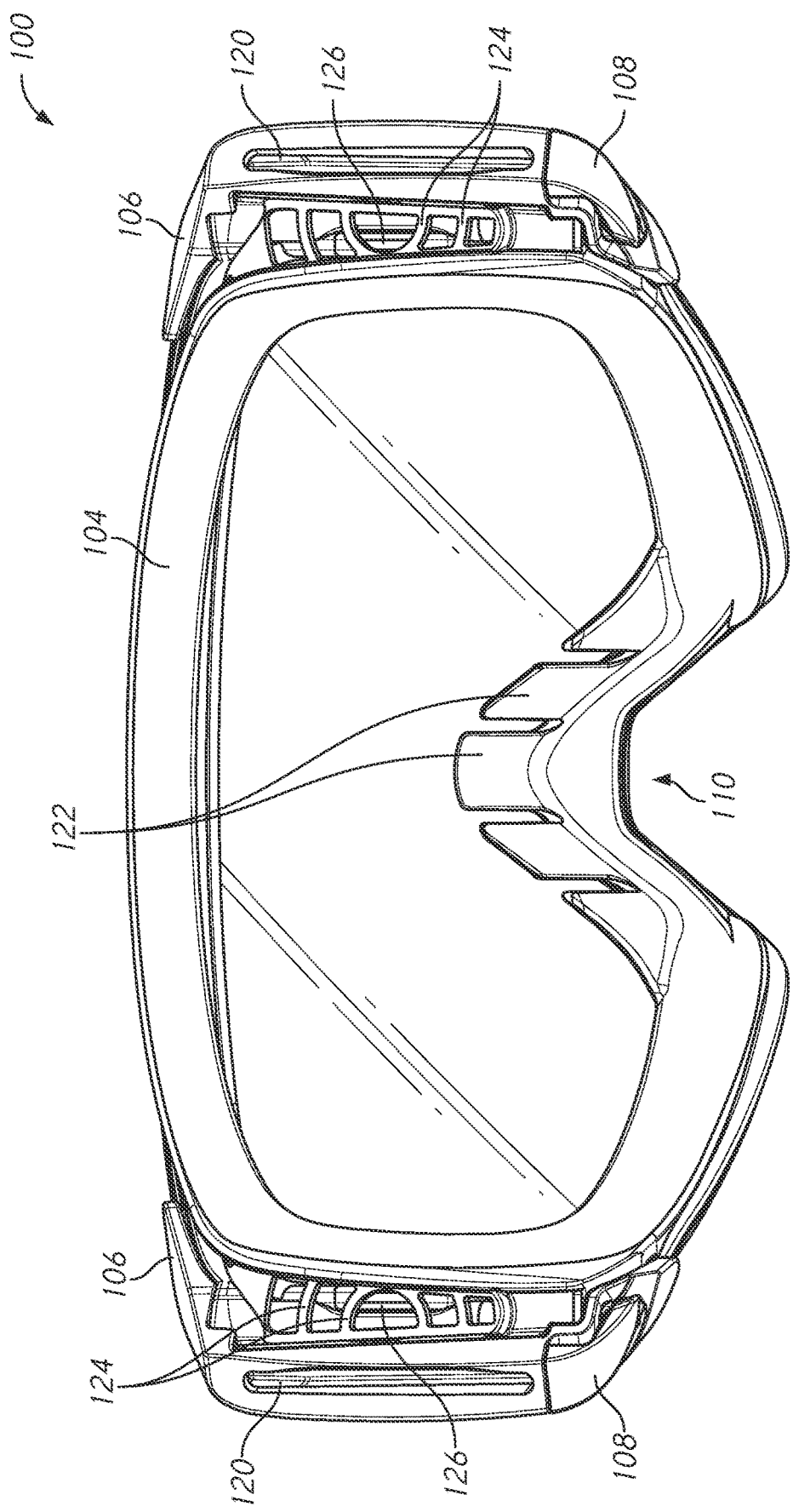
FIG. 3 is a rear view of the goggle in FIG. 1.

As shown in FIG. 1, an example goggle 100 includes a goggle frame 102 removably coupled to a lens assembly 112. The goggle 100 may define a nose recess 110 in a lower portion 204 of the goggle 100 (e.g., along a bottom periphery of the lens assembly 112), which may be configured to accommodate the nose of the wearer when the goggle 100 is worn. The goggle 100 may include first and second (e.g., left and right) end portions 200-1, 200-2 located on opposite lateral sides of the goggle 100. The goggle 100 may include outriggers 106 at each end portions 200-1, 200-2. As shown in FIG. 3, the outriggers 106 may be operatively associated with the goggle frame 102 for coupling a strap 111 (see FIG. 21) to the goggle. For example, the outriggers 106 may each include a slot 120 for coupling a strap (not shown in FIG. 1), such as an elastic headband. The outriggers 106 may be pivotally coupled to the goggle frame 102, which implies that one or more components of an outrigger may be designed to pivot with respect to the goggle frame 102 such as about a vertical axis. In some embodiments, one or both of the outriggers 106 may be fixed to the goggle frame 102, meaning that they are not intended to be movable (e.g., pivotable) to the goggle frame 102 in normal use. In some embodiments, the strap of the goggle may be fixed to the goggle frame 102 without the use of outriggers, for example by fixing the strap directly to the goggle frame, the lens, the lens assembly, or any suitable combination depending on whether the lens is removable or not. In general, the goggle 100 may have an arcuate shape to conform to a user's face.

Figure 20:
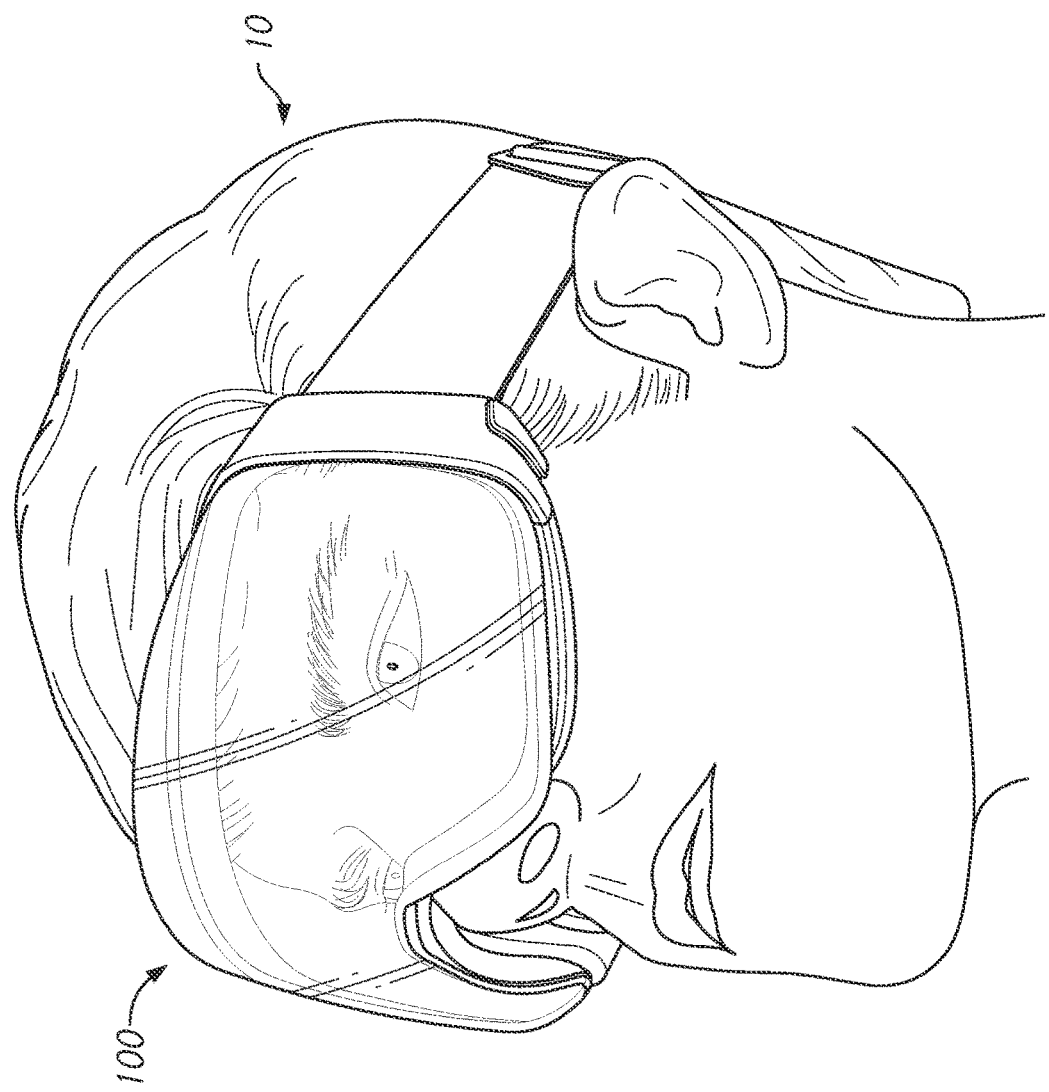
FIG. 20 shows an illustration of the goggle in FIG. 1 as worn by the user

With continued reference to FIG. 1, the goggle 100 may be of a shield-type design including one or more (e.g., inner and outer lenses) unitary lenses. The term "unitary lens" implies that a single lens extends in the field of view of both the left and right eyes of a user (see e.g., user 10 in FIGS. 20 and 21) when worn. Each individual lens may be formed from a single lens blank and may thus be devoid of any seams or other discontinuities in the lens. The one or more lenses (e.g., outer lens 114) may be made from polycarbonate (PC), acrylic, or other materials, which can provide suitable optical qualities (e.g., optical clarity) to the optical portion of the eyewear. The lens, or individual ones of the lenses such as in the case of a dual-lens design, may be coated and/or produced from lens materials (e.g., PC, acrylic, etc.) which are enhanced with a tint, polarization, mirror coating, antireflection, antifogging, impact or shatter resistance, or other treatments which may enhance the performance of the lens. The term "dual-lens" design implies that the lens assembly includes a pair of (i.e. inner and outer) unitary lenses, which are spaced apart from one another to reduce fogging. The lens assembly may be rimless or frameless in that a perimeter of the outer lens 114 is not substantially enclosed by a frame as illustrated in FIG. 1. The rimless design, in combination with the complex or compound curvature of the lens(es) according to the present disclosure, may provide substantially unobstructed view in a larger field of view for the user 10 (see FIG. 22), including in a downward direction (toward the ground), which is often obscured in existing goggles with conventional goggle lens and frame designs. In particular, the complex curvature of a goggle lens(es) combined with a unique cooperating shape of a goggle frame that supports the goggle lens(es), as described herein, may provide an enhanced (or enlarged) downward field of view as compared to conventional goggles.

To facilitate understanding of the compound curvature of the lens, a vertical or meridian line Y and a horizontal or longitudinal line X are shown with respect to outer lens 114. While this description is provided with reference to the outer lens, in dual-lens embodiments, the inner lens may have similar configuration. Typical goggle lenses are either cylindrical or spherical (e.g., made from a cylindrical or spherical lens blank, respectively). A cylindrical lens has a substantially constant curvature in the longitudinal direction and substantially no curvature in the vertical direction. In other words, the curvature of the lens along any X line (between the top and bottom edges of the lens) is substantially the same and all vertical Y lines (between the two lateral edges of the lens) have substantially no curvature. A spherical lens, on the other hand, has substantially the same curvature in both the longitudinal and vertical directions. In contrast, the goggle lens of the present disclosure cannot be described as being either cylindrical or spherical. That is, while one portion (e.g., an upper portion) of the goggle lens may be characterized as either cylindrical or spherical, at least one other portion (e.g., a lower portion) of the goggle lens cannot be characterized as cylindrical or spherical.

As illustrated, the curvature of the goggle lens (e.g., outer lens 114) may vary at least along a portion of one or more of the vertical (or meridian) lines, e.g., with the medial meridian indicated by line Y. For example, the lens (e.g., outer lens 114) may have a first radius of curvature, when measured along a meridian, in one portion of the lens, such as the upper portion of the lens, and it may have a second radius of curvature different from the first radius of curvature along the same meridian in a different portion of the lens, such as the lower portion of the lens. Moreover, the curvature of the lens along a particular meridian or the way the curvature varies along that meridian may differ from meridian to meridian. In some examples, the curvature of the lens measured along a given meridian may be substantially constant in a first portion, such as the upper portion, of the lens while the curvature of the lens, measure along the same meridian, may be variable in a second portion, such as the lower portion. The curvature of the lens in the first portion may be substantially constant along all meridians, while the curvature of the lens in the second portion may vary from meridian to meridian. In other words, different curvature profiles of the lens may be defined at different meridian sections through the second (e.g., lower) portion of the lens. The goggle lens may thus be referred to as having a complex or compound curvature. In other words, the term complex or compound, when describing the curvature of the goggle lens, may be understood to imply that the lens cannot be characterized as having either substantially spherical or substantially cylindrical surface across the full surface (e.g., the front or rear surface) of the lens. Configuring the goggle lens(es) to have a compound curvature as described herein may provide certain advantages, such as enabling a given portion of the lens (e.g., the lower portion of the lens) to be brought closer to the user's face (e.g., to the user's cheeks) to provide an enlarged field of view in the downward direction without substantially impacting the optical performance of the lens in the forward direction. Another technique for bringing the lower portion of a lens towards the user's face is configuring the goggle frame to hold the lens such that, when worn, the lens is tilted in the downward direction. However, tilting a conventional lens such as a cylindrical or spherical lens, downward may misalign the optical axis (e.g., the axis normal to the optical surface) of the lens from the forward line of sight, which may negatively impact the optical performance of the lens in the straight-ahead (or forward) viewing direction. Thus, a "tilting" technique may scarify performance in the forward viewing direction to potentially gain some additional field of view in a downward direction. In contrast, despite potential complexities in manufacturing a compound curvature lens of the kind described herein, the compound curvature lenses of the present disclosure may provide the advantage of enhanced downward field of view without the disadvantage of misaligning the optical axis of the main (or upper) portion of the lens from the forward viewing direction.

Referring to the specific illustrated example in FIG. 1, the outer lens 114 may have varying degrees of curvature along the vertical (or meridian) direction, e.g., as indicated by the exemplary medial meridian line Y. For example, an upper portion of outer lens 114 above line X may have a first radius of curvature. In some examples, the lens may have a substantially constant curvature along the upper portion (above line X) of each meridian. For example, the upper portion of the lens may correspond to a portion of a substantially cylindrical or spherical lens. A lower portion of outer lens 114 below line X may have a different radius of curvature from that of the upper portion. The curvature of the lower portion of the lens may be greater than that of the upper portion. In some examples, the lower curvature may be substantially constant in the region below line X or it may vary (e.g., increasing from line X toward the lower edge of the lens). In some embodiments, the curvature at the lower portion may correspond to a freeform curve (or spline) rather than being definable using a standard curve form (e.g., a quadratic curve form). In some embodiments, the maximum point of curvature of the lens is located below the optical center of the lens. Such configuration may allow the lower portion of the lens to wrap more tightly under the frontal portion of the lens and towards the user's cheeks thereby providing a larger unobstructed downward field of view as compared to conventional spherical or cylindrical lenses. In one example, the upper portion of the lens may have a radius of curvature of about 350 mm (or 1.5 base curve), while the lower portion, at the location of maximum curvature may have a radius of curvature of about 20 mm (or about 26 base curve). Different combinations of upper and lower curvatures may be used in other examples, such as an upper base curve of about 2 or up to 3.5 in some examples. As described, the radius of curvature of the lower portion may vary along the lower portion of the meridian line and/or between different meridians (e.g., the lower portion near the nose area may exhibit a larger radius of curvature and thus a smaller base curve as compared to the location of maximum curvature, which may be located near the side edges of the lens). The radius of curvature of the lower portion of the outer lens 114 may vary along a direction parallel to line X and/or in a direction parallel to line Y. The varying degree of curvature of outer lens 114 along line Y may provide a user with a greater field of view when the user is looking in a downward direction when wearing the goggle 100. The varying degree of curvature of outer lens 114 along line Y may provide aesthetic functions, for example, the appearance of the outer lens 114 may appeal to a user. In some examples, the radius of curvature along line X may be substantially constant.

Figure 18:
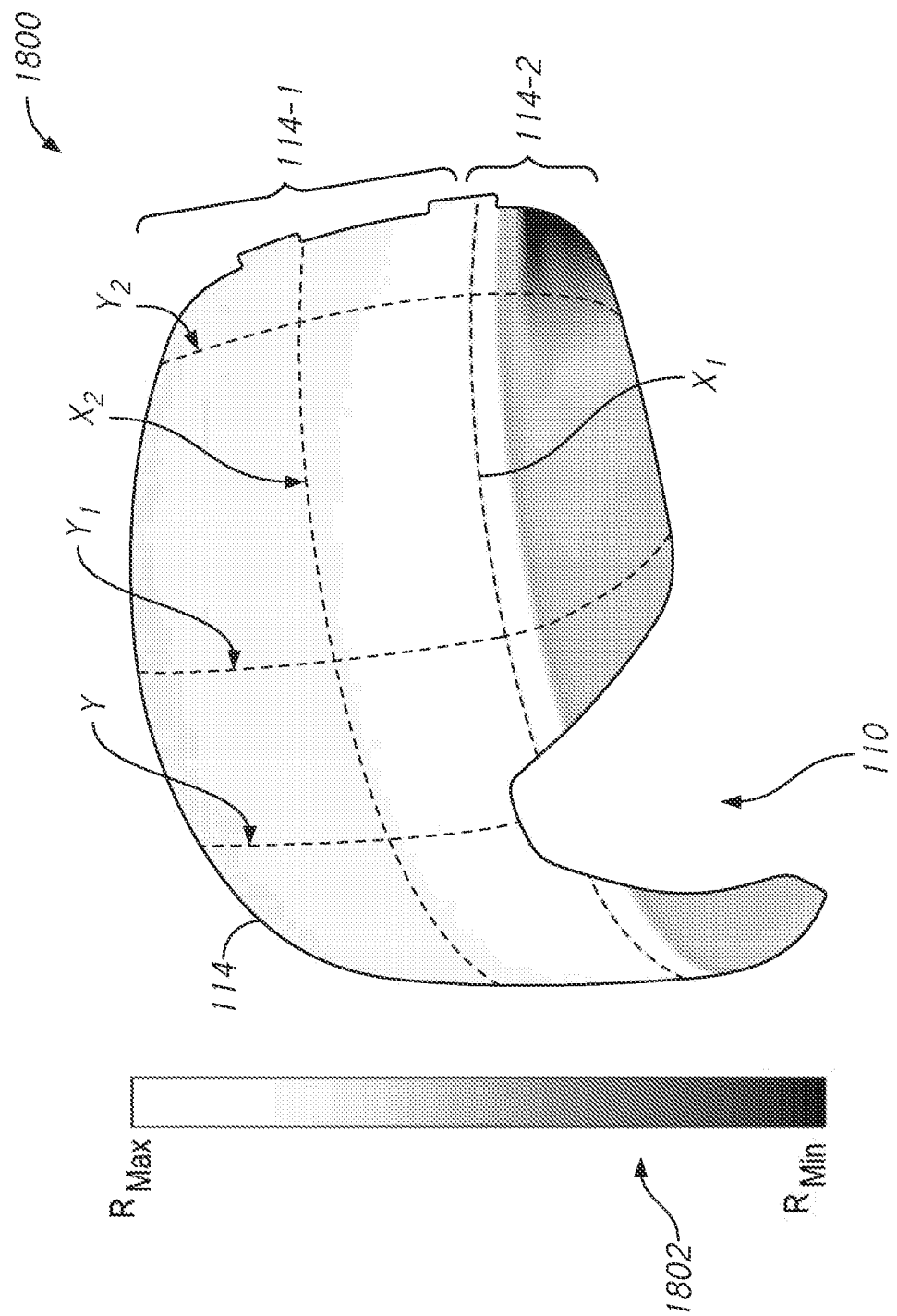
FIG. 18 is a color map of a view of a lens in accordance with some examples of the present disclosure.

An example of such variations in curvature may be more easily perceived with reference to the curvature "color map" shown in two exemplary different views 1800 and 1900 in FIGS. 18 and 19, respectively. The color map is overlaid on the surface of an exemplary lens, such as outer lens 114, to illustrate, in the form of a grayscale gradient, the radius of curvature at any given location along the convex outer surface of the lens. The inner surface of the same lens (e.g., outer lens 114) may have a substantially similar but concave shape. In some embodiments, the lens body may have a substantially constant thickness or be slightly tapered, with the thickness of the lens decreasing from the geometric center of the lens body to the outer periphery of the lens. In the color map in FIGS. 18 and 19, which show a front bottom isometric view 1800 and a side view 1900, respectively, of the outer lens 114, the darker grays correspond to greater degrees of curvature (i.e., a smaller radii of curvature), as indicated by the color bar 1802. As shown in FIGS. 18 and 19, the radius of curvature (R) of the upper portion 114-1 of outer lens 114, measured at any location along a meridian (e.g., $Y_1$, $Y_2$, $Y_n$), is substantially constant and is larger than the radius of curvature of the lower portion 114-2 of the lens 114, measured at locations along the same meridian. The radius of curvature measured at any location along a longitudinal line (e.g., $X_1$, $X_2$, $X_n$) in the upper portion 114-1 of the lens 114 is substantially constant, and in this case is also the same as the radius of curvature along the meridians in the upper portion 114-1, whereby the upper portion 114-1 of the lens 114 of this example can be described as spherical. In contrast, the horizontal radius of curvature in the lower portion 114-2 may not be substantially constant nor substantially the same as the horizontal radius of curvature in the upper portion 114-1, thus the lower portion 114-2 cannot be described as spherical nor cylindrical While the upper portion 114-1 of the outer lens 114 in this example is generally spherical, in other examples, the upper portion 114-1 may have a different regular shape (e.g., a cylindrical shape, which would imply that the meridian lines are substantially straight lines rather than curved lines).

The radius of curvature in the lower portion 114-2 may vary in one or both the horizontal and meridian directions, as indicated by the different shades of gray of the color map. As shown in FIGS. 18 and 119, the curvature of the lower portion 114-2 of the lens in a direction parallel to line X (e.g., different longitudinal lines) may vary. For example, darker shades of gray, which indicate greater amount of curvature (i.e., smaller radius of curvature) may be seen near the side or lateral edges of the lower portion 114-2 compared to the lower portion 114-2 near the nose recess 110, which are shown in lighter shades of gray thus indicated smaller amount of curvature (i.e., larger radius of curvature). In addition to defining a curve with varying curvature, the curves defined by different longitudinal lines may differ. That is, a longitudinal curvature in the lower portion 114-2 of the lens closer to the bottom edge may be the same (e.g., characterizable by the same mathematical form) as a longitudinal curve in the lower portion 114-2 of the lens closer to the upper portion 114-1. It will be understood that while some longitudinal curves in the lower portion 114-2 may define a varying radius of curvature of the lens, it is not necessary that all longitudinal curves in the lower portion 114-2 define a varying radius of curvature of the lens.

The curvature in a direction parallel to line Y (e.g., along a same meridian) may also vary in the lower portion 114-2 of the lens 114. For example, darker shades of gray may be seen near the bottom edge of outer lens 114 compared to a portion of the outer lens 114 near line $X_1$, which may delineate the upper portion 114-1 from the lower portion 114-2. As can be perceived, the region which includes the greatest degree of curvature may be located in the lower portion and in some cases towards the lateral edges of the lens, and thus outside of the main field of view (e.g., when the user is looking straight ahead and/or straight down). Any perceivable distortion as may results from large radii of curvature may thus be contained only in or limited to the peripheral region of the lens. The curvature maps shows in FIGS. 18 and 19 are provided only to illustrate an example of complex curvature, which may be used in embodiments in accordance with the present disclosure without limiting the present scope. In other embodiments, the location(s) of maximum curvature may be located elsewhere in the lower portion of the lens, or elsewhere altogether.

Figure 2:
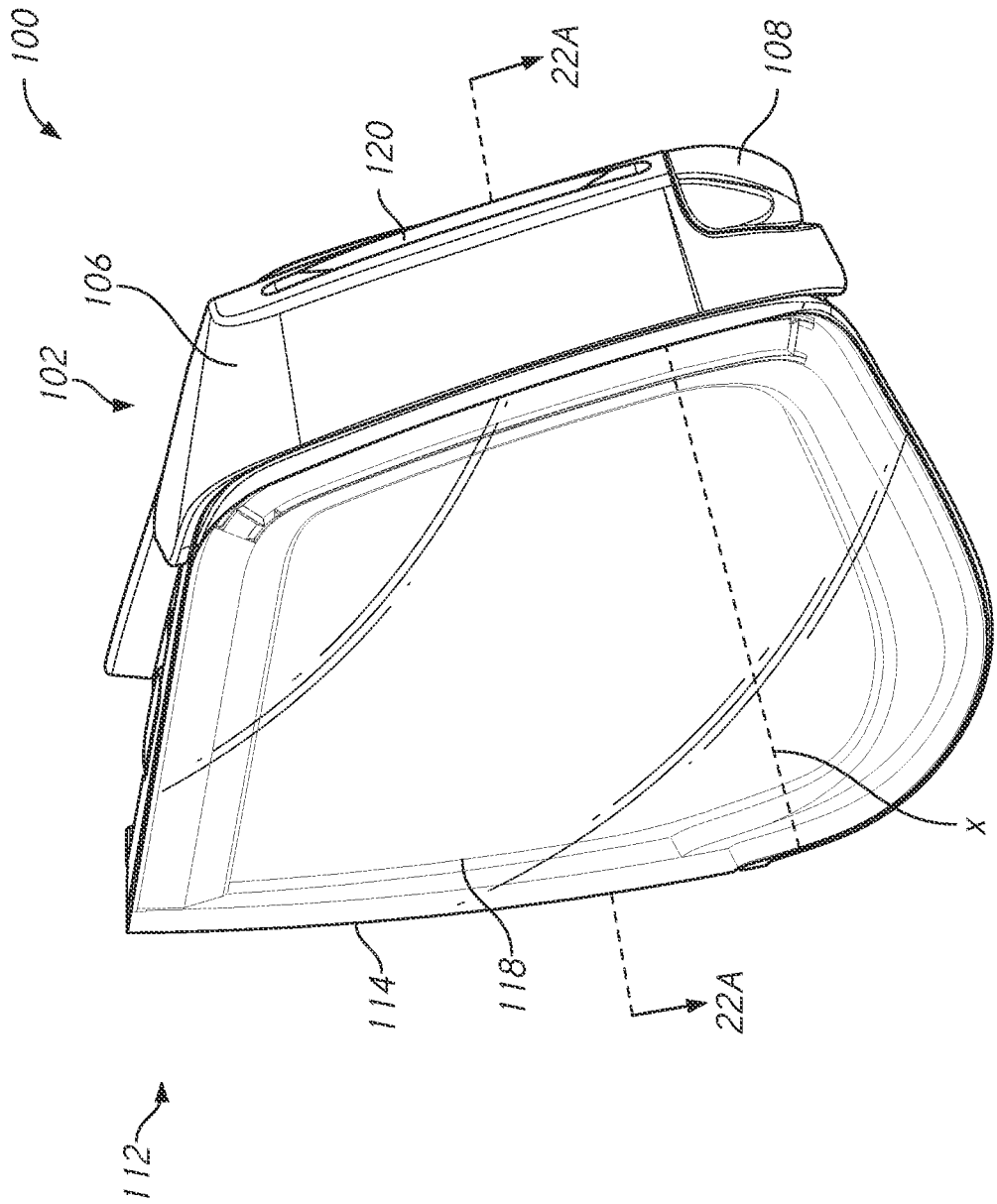
FIG. 2 is a side view of the goggle in FIG. 1.

In some embodiments, the lens assembly 112 may include a dual-lens structure. For example, as illustrated in FIGS. 2 and 4, the lens assembly 112 may include outer lens 114 and inner lens 118. In some embodiments, the shape and thus the curvature of the inner lens 118 may be substantially similar to the curvature of the outer lens 114. The lenses 114 and 118 may comprise one or more compounds and/or coatings configured to impart light transmittance characteristics as may be desired or suitable for a particular application. For example, the lenses 114 and 118 may include one or more compounds or coatings, which configure the lenses 114 and 118 into a tinted lens, a polarized lens, a scratch resistant lens, or combinations thereof. Additionally or alternatively, the lenses 114 and 118 may be formed from a projectile- or shatter-resistant material selected to meet one or more ballistic safety standards. The lenses 114 and 118 may have a front or outward-facing surface (i.e. the side of the lenses, which is farthest away from the user's face when the eyewear is worn) and a rear or inward-facing surface (i.e. the side of the lens, which is closest to the user's face when the eyewear is worn). Compounds and/or coatings, such as for tinting the lenses 114 and 118, may be laminated in the body of the lenses 114 and 118 and/or applied to either of the rear or front sides of the lenses 114 and 118. In some embodiments, inner lens 118 may be formed of a different material than the outer lens 114. For example, the inner lens 118 may be designed to be hydrophilic to inhibit fogging. In some embodiments, for example, as seen in FIG. 4, the inner lens 118 may be smaller in size (e.g., height and/or thickness) than the outer lens 114. In an example manufacturing process, the lenses may be produced by forming custom-shaped blanks (e.g., for each of the inner and outer lens) from which the lens, in its final shape may be cut (e.g., to define the nose recess, and the side edge geometry including the lens tabs in examples which include lens tabs). Other suitable manufacturing processes may be used, such as forming the lens to its final shape and outline with minimal cutting/removal of material involved.

Returning to FIG. 1, the lens assembly 112 may include lens frame 116. In some examples, the lens frame may be formed from a flexible material (e.g., an elastomer such as thermoplastic polyurethane (TPU)). That is, the lens frame 116 may be resilient and relatively softer than conventional lens frames made out of relatively rigid materials such as nylon. An elastomer lens frame 116 may allow the lens assembly 112 to form a better seal with goggle frame 102. An elastomer lens frame 116 may improve conformity of the lens assembly 112 to a user's face. Additionally, as further described below, at least one of the lenses (e.g., outer lens 114) may be assembled to the lens frame by a portion of the lens frame wrapping around an edge of the lens. Thus, a lens frame made of a resiliently flexible material such as an elastomer may facilitate the assembly process of the lens to the lens frame. The lens frame 116 may attach the outer lens 114 and inner lens 118 together (e.g., functioning also as a spacer). In the example in FIGS. 1 and 4, the outer lens 114 is positioned on one side of the lens frame 116 and the inner lens 118 is positioned on the opposite side of the lens frame 116, the lens frame 116 extending along a peripheral portion of the outer lens 114 and inner lens 118 so as to provide a large unobstructed field of view through the outer lens 114 and inner lens 118. In the illustrated embodiment, the lens frame 116 is coupled to the outer lens 114 and inner lens 118 such that no separate spacer is used. In other embodiments, a separate spacer may alternatively or additionally be used to provide the two lenses in the spaced apart configuration to define an interstitial space between the two lenses. In some such examples, the lens frame may be coupled to the outer lens only or the inner lens only, while the two lenses may be coupled to one another using a spacer.

Figure 5A:
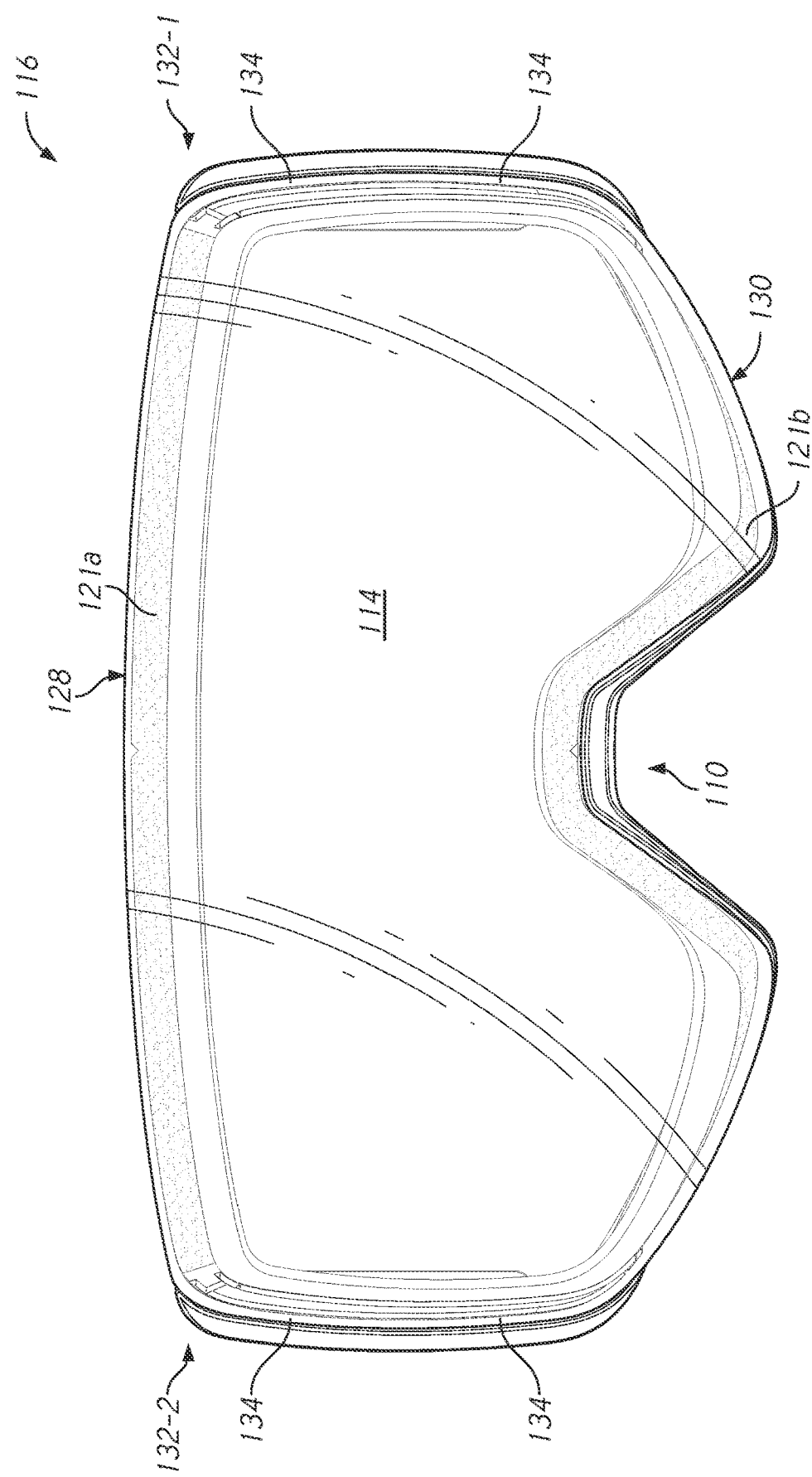
FIG. 5A is a front view of a lens assembly of the goggle in FIG. 1.
Figure 5B:
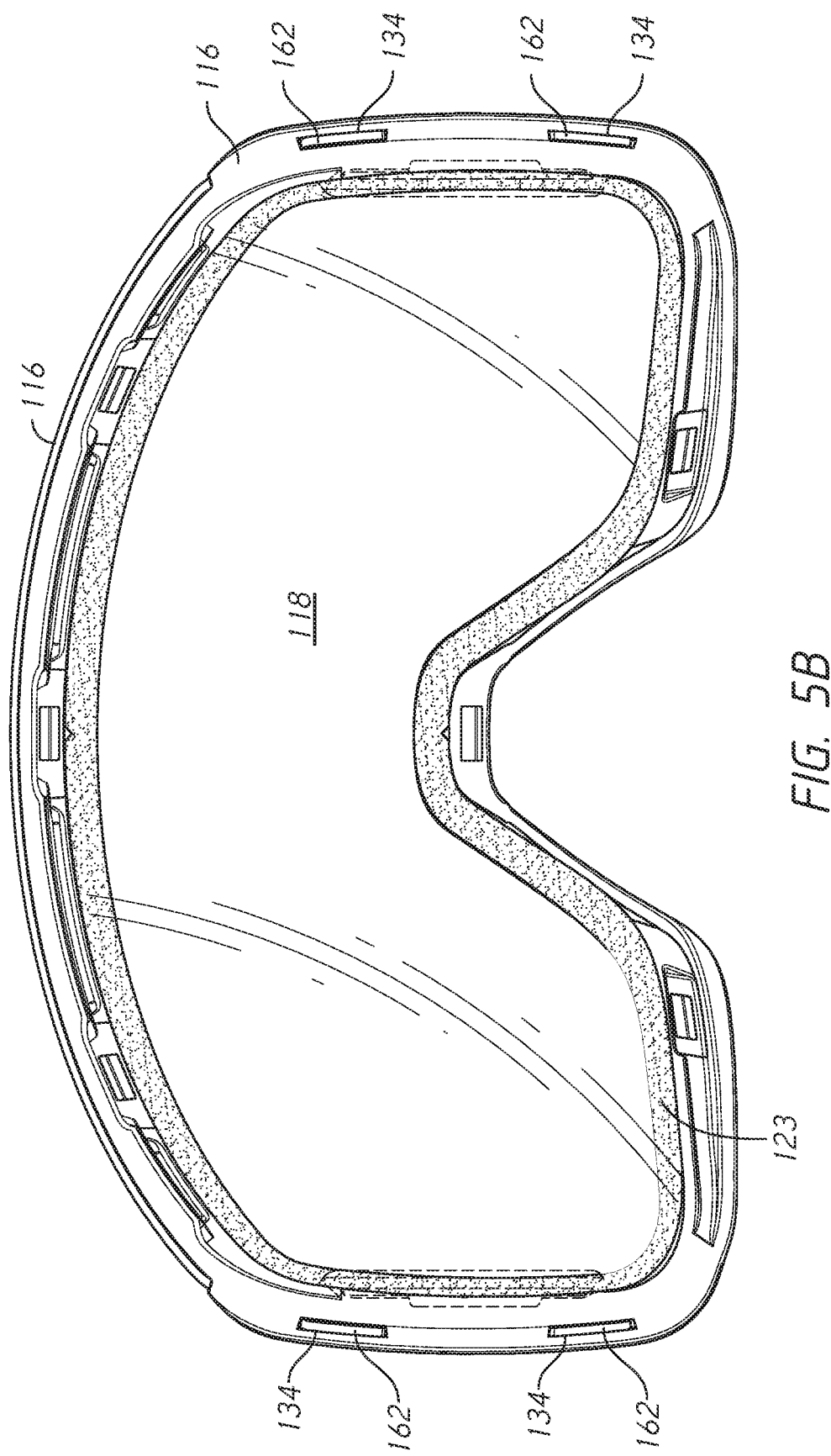
FIG. 5B is a rear view of the lens assembly in FIG. 5A

Referring to FIG. 5A, the lens frame 116 may include upper portion 128, lower portion 130 and side portions 132-1, 132-2. In some embodiments, one or both of the lenses may be fixed (e.g., adhered) to the lens frame 116 along only a portion of the perimeter of the respective lens. For example, as shown in FIG. 5A, the outer lens 114 may be fixed (e.g., adhered for example using tape adhesive 121a and 121b) along only the upper and lower portions 128 and 130, respectively, of the frame. The lens 114 may not be fixed to the lens frame 116 along the side portions 132-1 and 132-2. Instead, each of the left and right lateral edges of lens 114 may be received in a corresponding one of the slits 134 located at each side portion 132-1, 132-2 of the lens frame 116. No adhesive may be applied between the side portions 132-1, 132-2 of the lens frame 116 and the lateral peripheral edges of the lens 114. In some embodiments, the adhesive may be a tape that has an adhesive on both sides of the tape. An example of an adhesive tape that may be used is VHB Tape manufactured by 3M. As shown in FIG. 5B, the inner lens 118 may be fixed to the lens frame 116 along substantially the full perimeter of the lens, for example using tape adhesive 123, which may be of the type described above, or other suitable means. In other embodiments, the outer lens 114 may also be fixed to the lens frame 116 along substantially its full perimeter.

Figure 6:
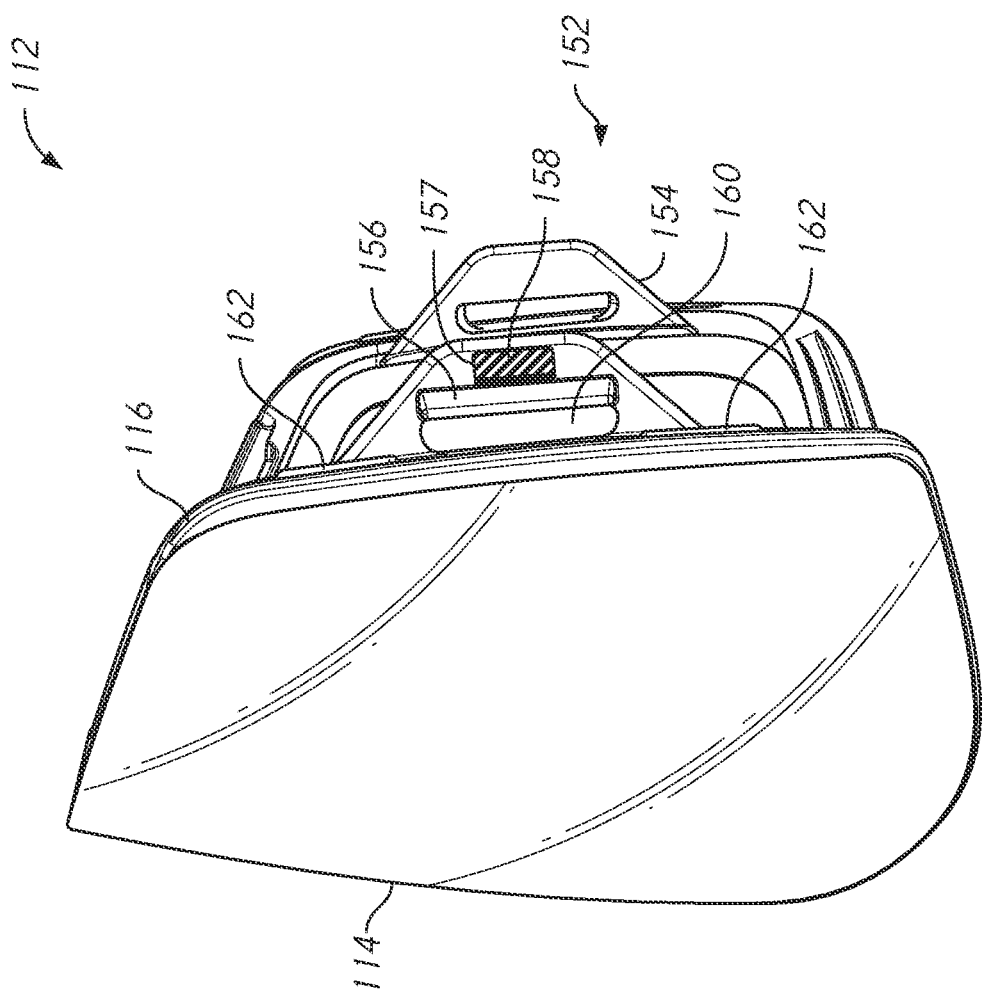
FIG. 6 is a view of a lens assembly in accordance with some of the examples of the present disclosure.

As shown in FIG. 6, outer lens 114 may include one or more lens tabs 162 at a periphery of the outer lens 114, for example at a lateral edge of the lens 114. The lens tabs 162 may be received in corresponding slits 134 of the lens frame 116 such that the engagement between the lens tabs 162 and slits 134 secure the outer lens 114 to the side portions 132-1, 132-2 of the lens frame 116.

Figure 7:
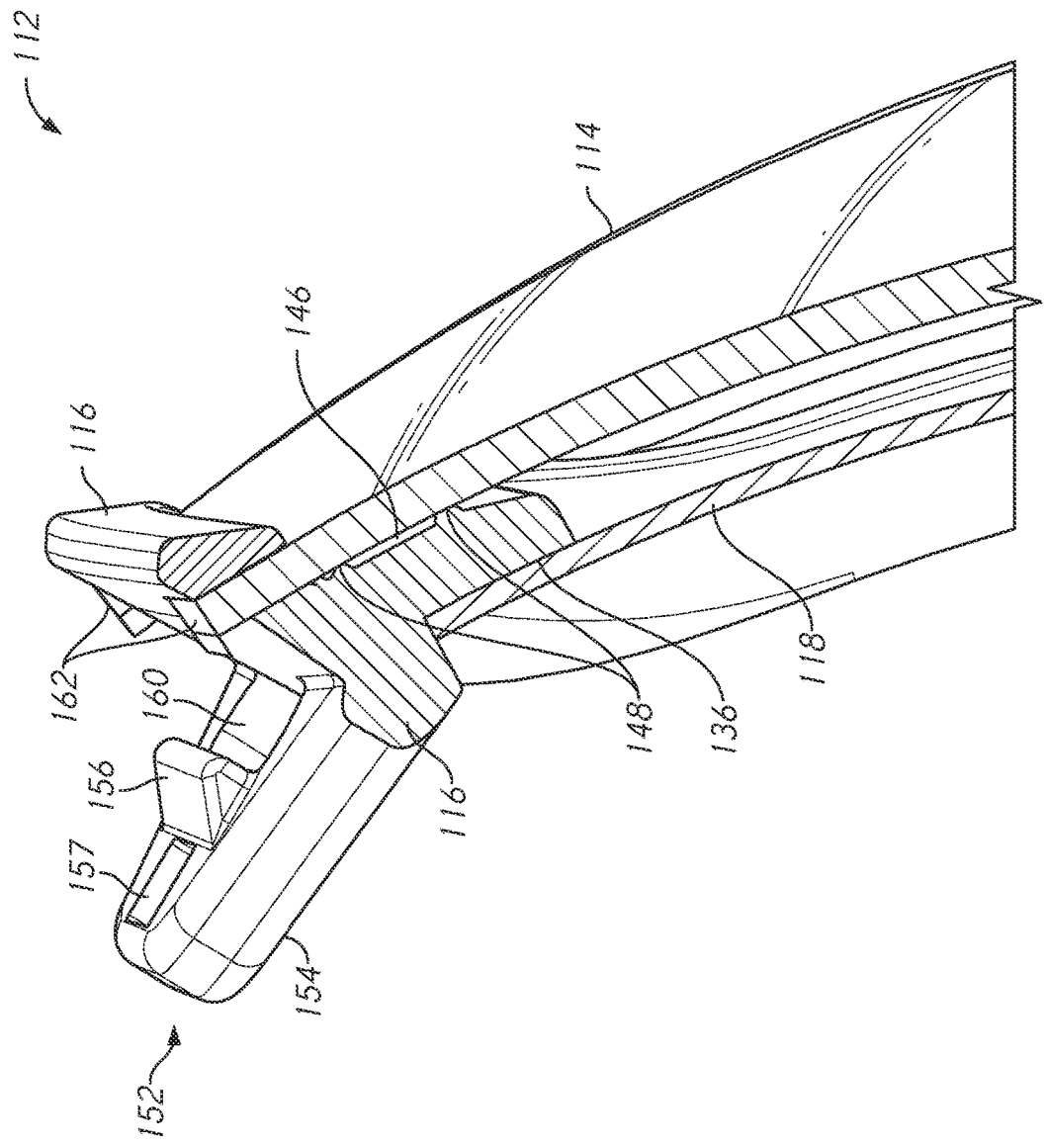
FIG. 7 is a sectional view of a lens assembly in accordance with some examples of the present disclosure.
Figure 9:
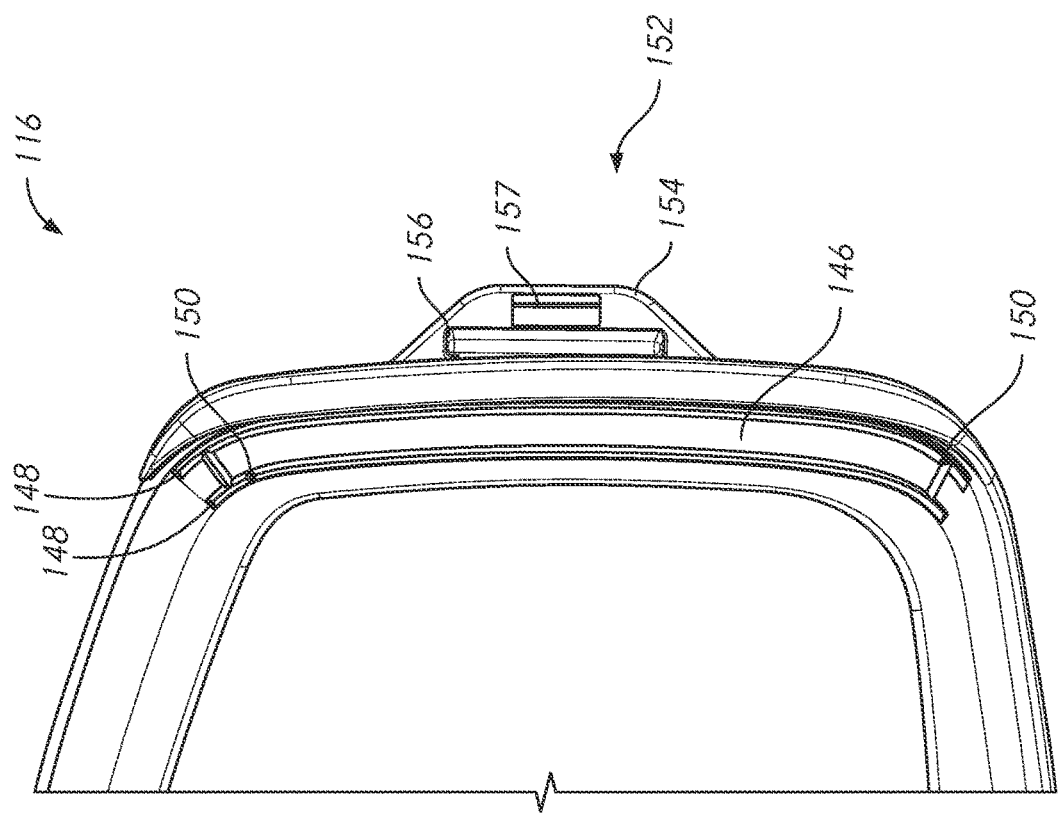
FIG. 9 is a view of a lens frame in accordance with some examples of the present disclosure.

Referring to FIGS. 7 and 9, in some embodiments, the lens frame 116 may include a channel 146 along each end portion 132-1, 132-2. The channel 146 may be defined by a pair of spaced apart ridges 148, which may extend along some or substantially the full length of the end portions 132-1 and 132-2 (see also FIG. 9). In the example in FIG. 9, each of the ridges 148 in a pair extends substantially continuously from the upper portion to the lower portion of the lens frame to provide a raised contact surface (raised above surface 133) for contacting the rear surface of the outer lens 114. As such, the rear or inner surface of outer lens 114 may rest, along its lateral edges, on the raised surfaces provided by the ridges 148 rather than on the front surface 133 to which the adhesive 121a and 121b is applied. In some embodiments, the ridges 148 may help form a seal between the outer lens 114 and the lens frame 116 along the side portions 132-1, 132-2. In some embodiments, the ridges 148 may apply a force on the outer lens 114 that improves the retention of the lens tabs 162 in the slits 134.

Because goggles are often used during exertion by the users (e.g., snow sports, or other sport or strenuous activity), fogging of the goggle lens may occur. Dual-lens structures are often used to reduce fogging. Dual-lens structures are often equipped with a pressure equalization port that opens the interstitial space between the lenses to ambiance. In some existing goggles, to prevent the ingress of moisture in the interstitial space, which can increase the risk of fogging, a specifically designed port may be provided in the outer lens itself, which may be made more complex by the inclusion of a filter or other porous membrane that allows air to pass without the passage of moisture. In accordance with the principles of the present disclosure, a multi-functional vent port may be provided by a pair of misaligned holes 150, each formed in a respective one of the ridges 148 in one of the pair of ridges. In some embodiments, a vent port may be formed in both pairs of ridges at each of the side portions 132-1, 132-2 of the lens frame 116. As shown in the example in FIG. 9, one of the ridges 148, for example the medial ridge of a given pair, may include a vent hole 150 near the upper portion 128 of lens frame 116 and the other ridge, for example the lateral ridge of the same pair, may include a vent hole 150 near the bottom portion 130 of outer lens 114. The specific vertical locations of the vent holes 150 are illustrative only and vent holes 150 may be positioned differently in other examples, such as with different spacing (or amount of vertical misalignment) and/or the location of the upper and lower vent holes may be switched as between the medial and lateral ridges 148. The pair of vent holes 150 may couple the interstitial space between outer lens 114 and inner lens 118 to allow air to pass into and out of the interstitial space between the two lenses. The vent port may provide an opening for pressure equalization and may also facilitation the circulation or exchange of air, which may reduce fogging between the outer lens 114 and inner lens 118. Arranging the vent holes at locations that are vertically misaligned may reduce the risk of ingress of moisture into the interstitial space between the outer lens 114 and inner lens 118. In some embodiments, the ridges 148 and vent holes 150 may be provided on a different surface of the lens frame 116 such that the ridges contact a surface of inner lens 118. While conventional goggle lenses typically have only a single vent hole that primarily functions for pressure equalization, using multiple vent holes 150, as in the present embodiment, may allow for air circulation or exchange.

Referring back to FIGS. 4 and 7, the lens frame 116 may include a ledge 136 on the rear side 135 for accepting the inner lens 118 when goggle 100 includes a dual lens structure. An adhesive may be applied along the ledge 136 to couple the inner lens 118 to the lens frame 116. In some embodiments, the adhesive may couple the inner lens 118 to the lens frame 116 along an entire periphery of the inner lens 118. In some embodiments, the adhesive used to couple the inner lens 118 to the lens frame 116 may be the same type of adhesive used to couple the outer lens 114 to the lens frame 116. In some embodiments, the ledge 136 may be configured such that the inner lens 118 may be press-fit into the lens frame 116 such that the lens 118 rests on the ledge 136 and the lens frame "grips" a periphery of the inner lens 118. The press-fit may further couple the inner lens 118 to the lens frame 116.

As shown in FIGS. 3 and 4, the goggle frame 102 may include a face gasket 104. The face gasket 104 may be provided by one or more resiliently deformable components, which are configured to be placed conformally to a user's face. The face gasket 104 may be formed of a flexible material such as thermoplastic polyurethane (TPU) or other suitable elastomer for conformally interfacing with the user's face. In some examples, foam (not shown here) may additionally be used to line portions (e.g., the web portion or simply web 181) of the face gasket, for example to substantially fill the space between the lens interfacing portion 177 of the face gasket 104 (e.g., along a front surface 173) and the user-facing side 175 of flange 179), which defines the top vent 174 of goggle 100.

Figure 10:
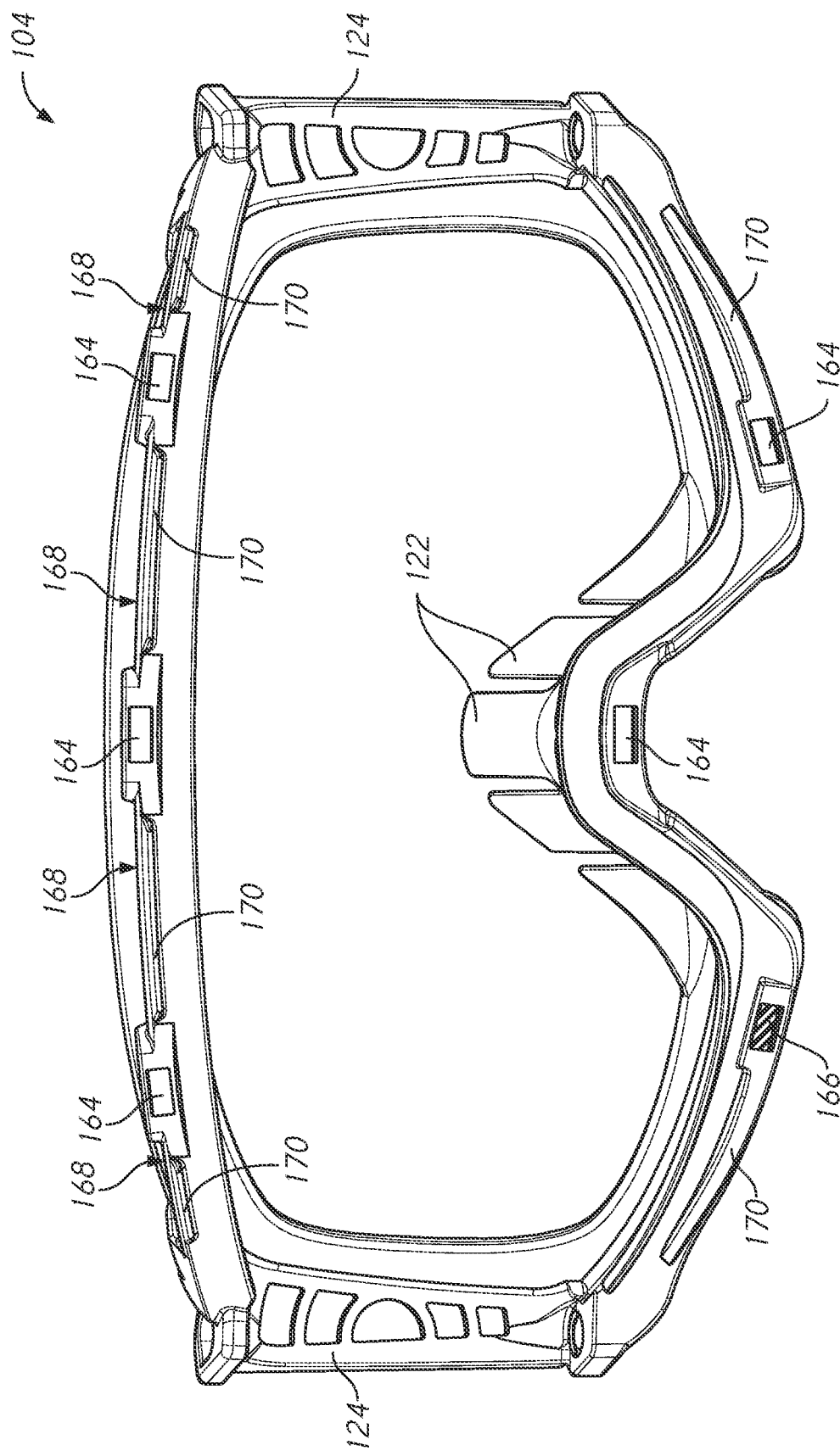
FIG. 10 is a front view of a face gasket in accordance with some examples of the present disclosure.

As shown in FIGS. 3 and 10, a lower portion of a flange of the face gasket 104 may include a nose rest 122 configured to conform to a user's nose for a comfortable fit. Although not shown in the figures, the nose rest 122 may optionally be coupled to a nose pad on a surface adjacent to a user's nose when the goggle 100 is worn. The nose pad may be formed from a soft for flexible polymeric material (e.g., foam) which may conform to the user's nose for a comfortable fit. The nose pad may optionally include one or more bendable portions for improved adjustability. In some examples, the nose pad may be removably attached to the nose rest 122 so that the nose pad can be replaced when desired by the user. As illustrated in FIG. 4, due to the compound curvature of the lens, which wraps closer to the user's face, the lower portion of the face gasket extends forward of the flange to a smaller extent than the upper portion thus essentially being devoid of a web portion in that region. In the lower portion, the flange 179, is substantially adjacent to and connected to the lens interfacing portion 177 of the face gasket, while in the upper portion of the face gasket, the flange 179 and lens interfacing portion 177 are spaced apart by the web 181. The web may, as in the illustrated example, include a plurality of cutouts (e.g., vent apertures of top vent 174 and/or side vents 124) allowing the flange portion to flex and conform to different face shapes and sizes without impacting the lens to frame interface, and which may also improve venting of the space between the inner lens and the user's face as described further below.

Figure 11:
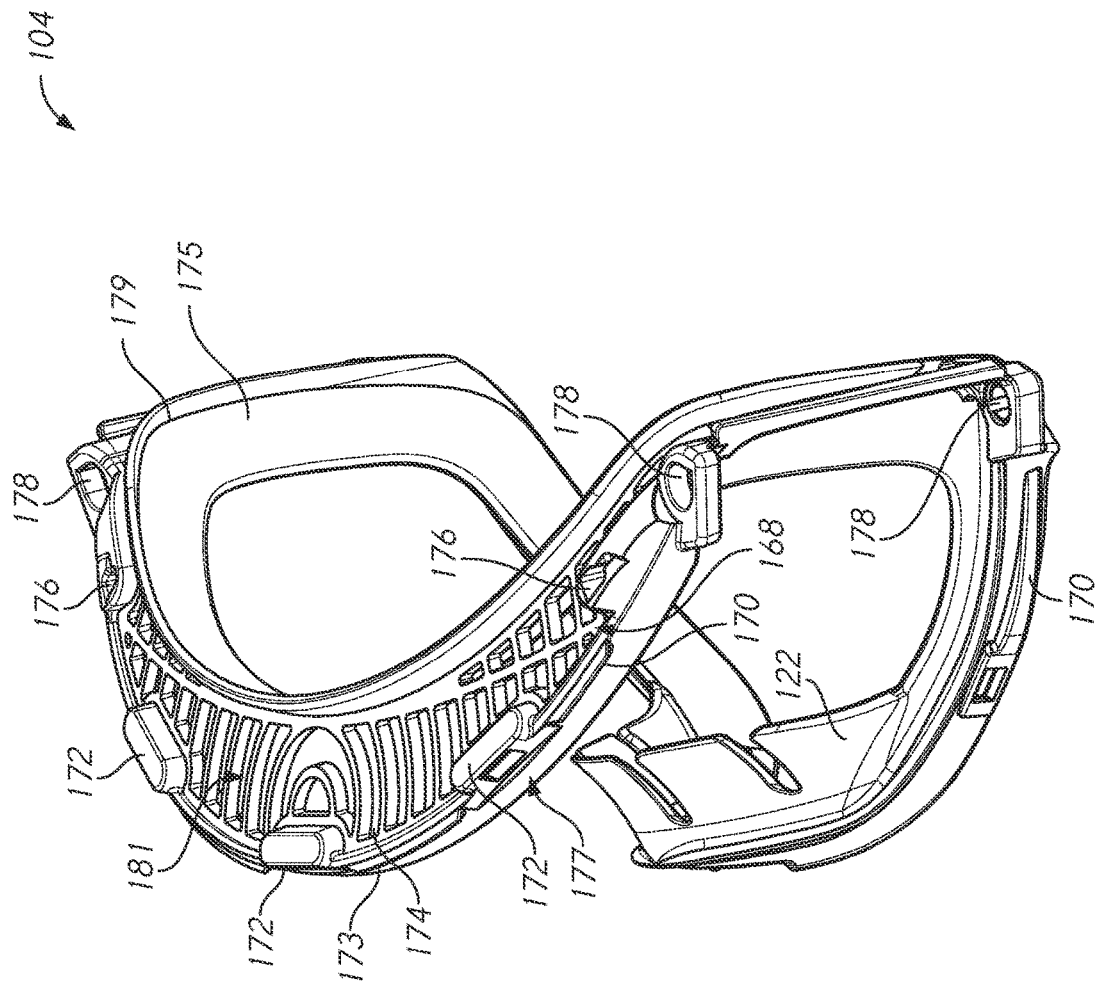
FIG. 11 is a view of the face gasket in accordance with some examples of the present disclosure.

Referring to FIGS. 10 and 11, the face gasket 104 may include one or more vent apertures that allows air to circulate between the face gasket 104 and a user's face when the goggle 100 is worn. Allowing air to circulate may prevent the portion of the user's face covered by the goggle 100 from becoming overheated, thus improving the comfort of goggle 100. Face gasket 104 may include side vents 124 at the end portions 200-1, 200-2 of the goggle 100. Face gasket 104 may further include a top vent 174 along an upper portion 202 of goggle 100. The top vent 174 may include one more apertures that extend through the thickness of the web 181, and which may extend, at least partially, between the flange 179 and the lens interfacing portion 177. Although not shown in the figures, side vents 124 and top vents 174 may be covered or partially covered by a porous and/or breathable polymeric material (e.g., foam). Covering the vents may still allow air to circulate between the goggle 100 and the user's face, but may protect the user's face from drafts and/or cold air temperatures (e.g., when skiing). Although not shown, some or all of rear surface 175 may be covered with a soft polymeric material (e.g., foam). This may improve comfort of the goggle 100 when worn on the user's face.

As can be seen in FIGS. 3 and 11, the face gasket 104 may include outrigger coupling holes 176 at end portions 200-1, 200-2 of the upper portion 202 of the goggle 100. The outrigger coupling holes 176 may be configured to accept hooks 188 (visible in FIGS. 4 and 11) of the outriggers 106. In some examples, the outriggers 106 may be fixedly attached to the face gasket 104. The flexibility of the face gasket 104 may allow the goggle 100 to still be worn comfortably by a user without pivotal outriggers. In some examples, the flexibility of the face gasket 104 and the lens frame 112 may allow the goggle 100 to be worn comfortably by a user without pivotal outriggers.

The goggle frame 102 may be magnetically coupled to the lens assembly 112. The lens assembly 112 and the goggle frame 102 may include magnetic materials (e.g., a permanent magnet such as a rare earth magnet, or ferromagnetic material such as iron or steel) for removably coupling the lens assembly 112 to the goggle frame 102. In some embodiments, the magnetic materials may have one or more surfaces exposed (e.g., the facing surfaces of the magnets). The magnetic materials may be substantially enclosed (e.g., except for one side of the magnetic material being at least partially exposed) in pockets formed within the lens assembly 112 and the goggle frame 102. The magnetic materials may be attached to opposing (e.g., facing) sides of the lens assembly 112 and the goggle frame 102 to urge the lens assembly 112 towards the goggle frame 102. The magnetic attraction between the magnetic materials on the lens assembly 112 and the goggle frame 102 may provide a centering function (e.g., resulting from the magnetic materials natural tendency to axially align their respective fields to one another), which may facilitate alignment of the lens assembly 112 to the goggle frame 102. In some examples, the face gasket 104 and lens frame 116 may include corresponding magnetic elements for magnetically coupling the goggle frame 102 to the lens assembly 112.

Figure 8:
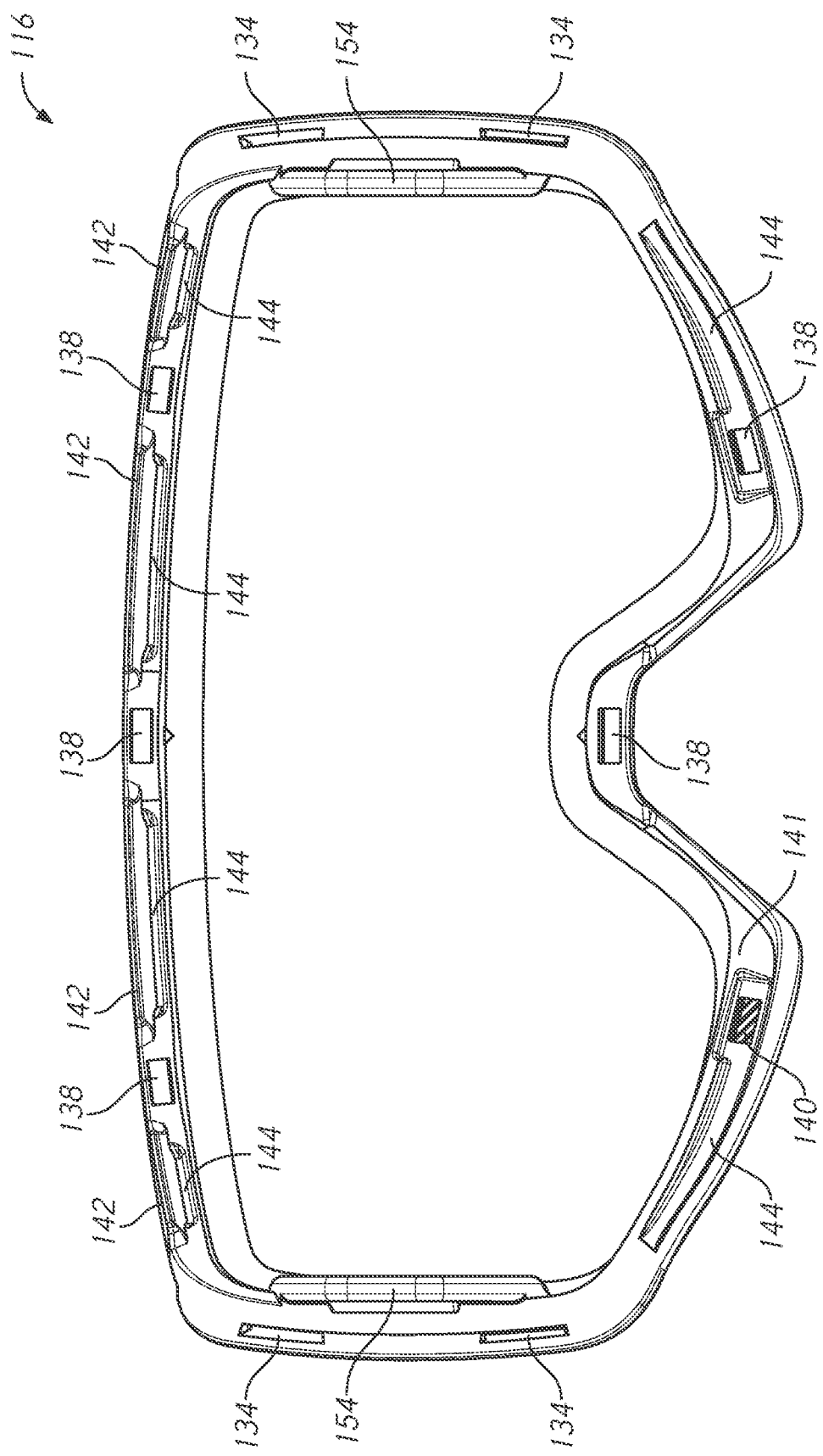
FIG. 8 is a rear view of a lens frame in accordance with some examples of the present disclosure.

Referring to FIGS. 8 and 10, the face gasket 104 may include magnetic elements 166 for magnetic coupling with corresponding magnetic elements 140 included with lens frame 116. For example, the face gasket 104 may include magnetic elements 166 exposed along front surface 173. The magnetic elements 166 may be arranged along a lower portion 204 of the goggle 100 (such as generally beneath a wearer's eyes and adjacent the wearer's nose) and along an upper portion 202 of the goggle 100 (such as adjacent a wearer's forehead). Several magnetic elements 166 may be arranged adjacent the nose rest 122. In the illustrated embodiment, the face gasket 104 includes six magnetic elements 166, but in other embodiments the face gasket 104 may include more or less than six magnetic elements 166. The magnetic elements 166 may include an exposed surface that is substantially flush with the front surface 173, which in some embodiments, may be angled inward and rearward toward a center of the goggle frame 102 to facilitate alignment of the lens assembly 112 with the goggle frame 102. In other embodiments, different arrangement (e.g., orientation) of the magnets with respect to the front surface 173 may be used.

Figure 23:
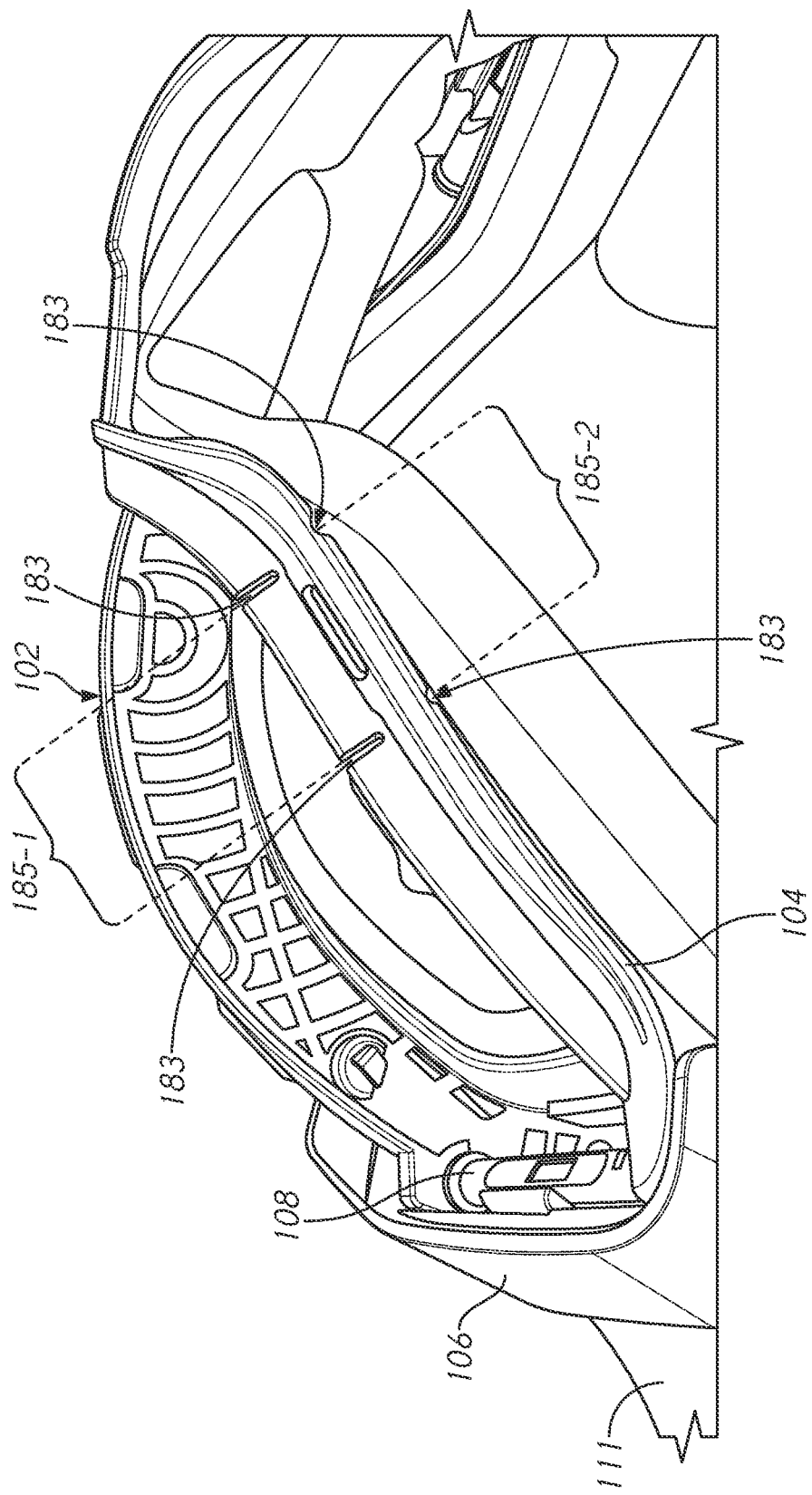
FIG. 23 shows a goggle frame according to the present disclosure illustrating stress isolation features on the goggle frame.
Figure 24:
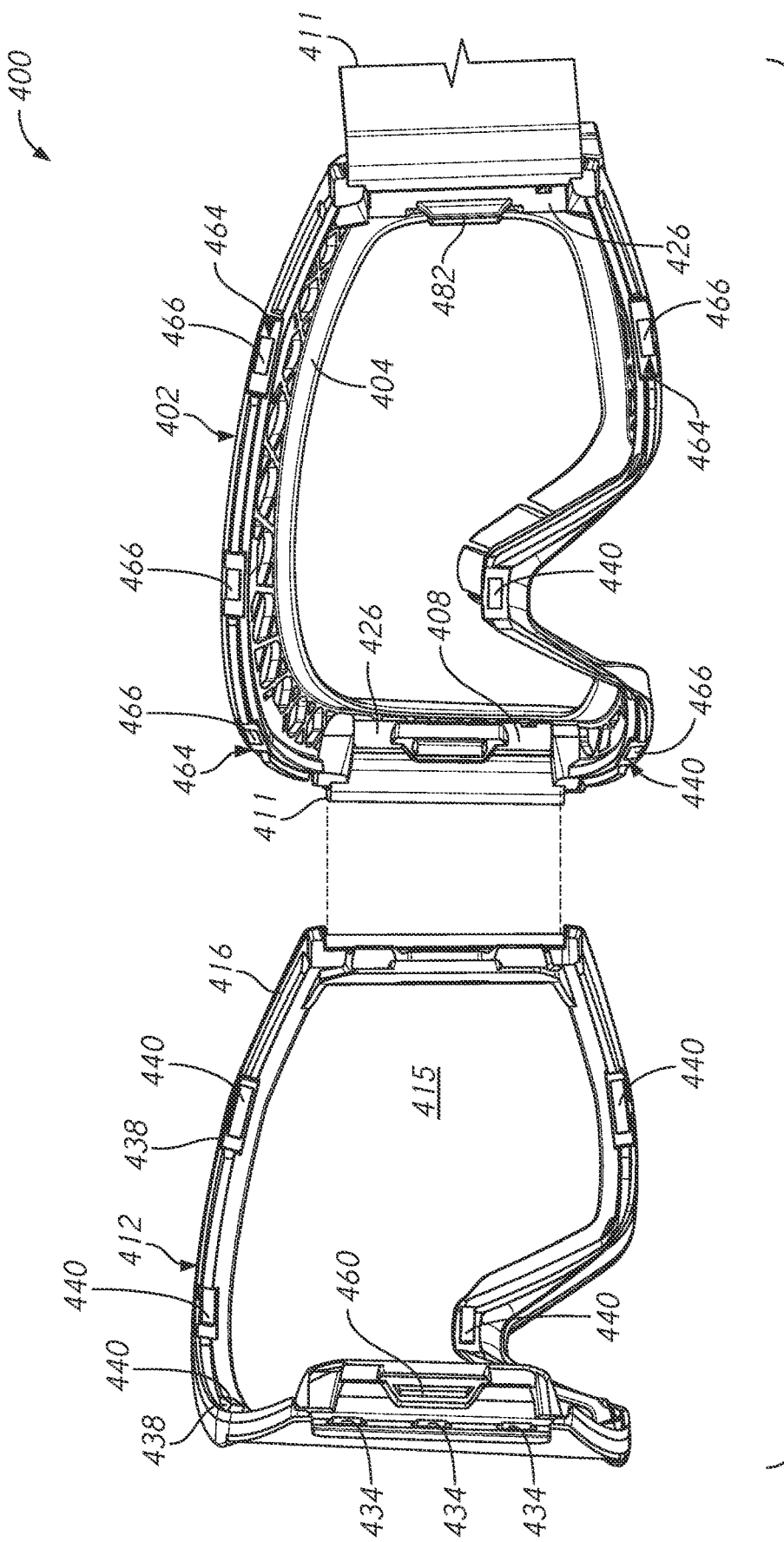
FIG. 24 shows a partially exploded view of another example of a goggle with a lens interchange system according to the present disclosure.
Figure 26B:
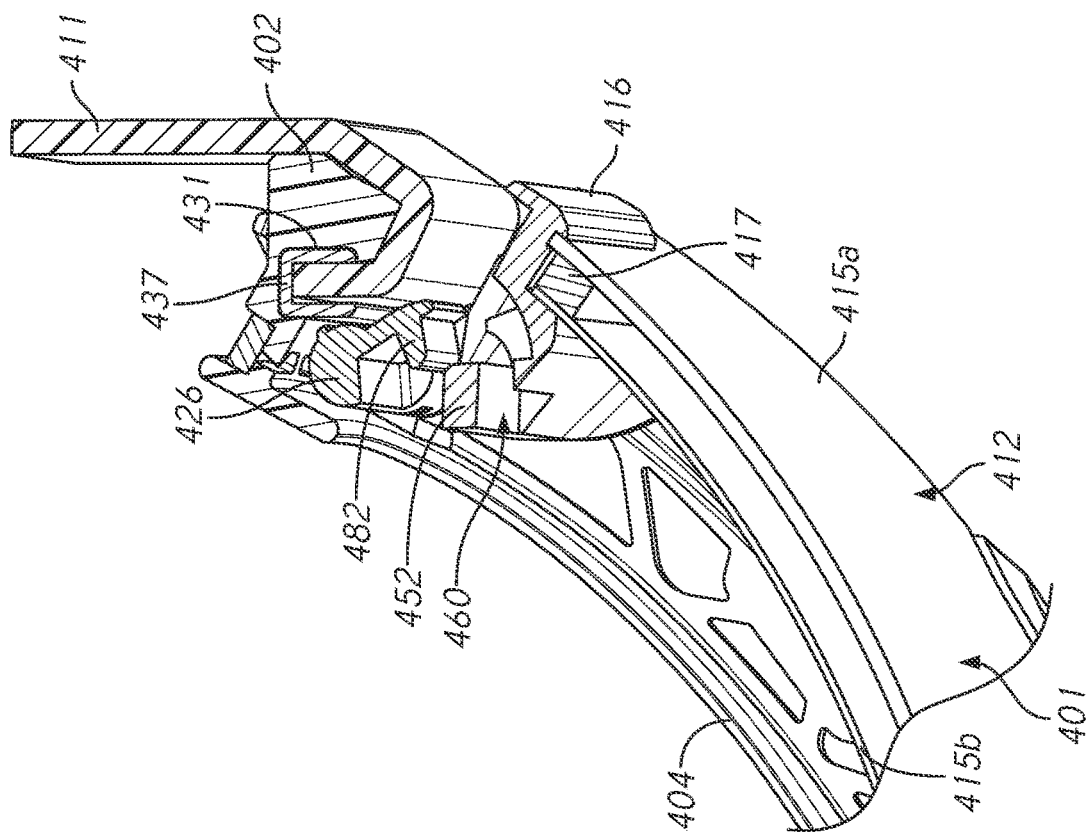
FIGS. 26A and 26B show partial cross-sectional views of the latch mechanism of the goggle in FIG. 24.
Figure 26A:
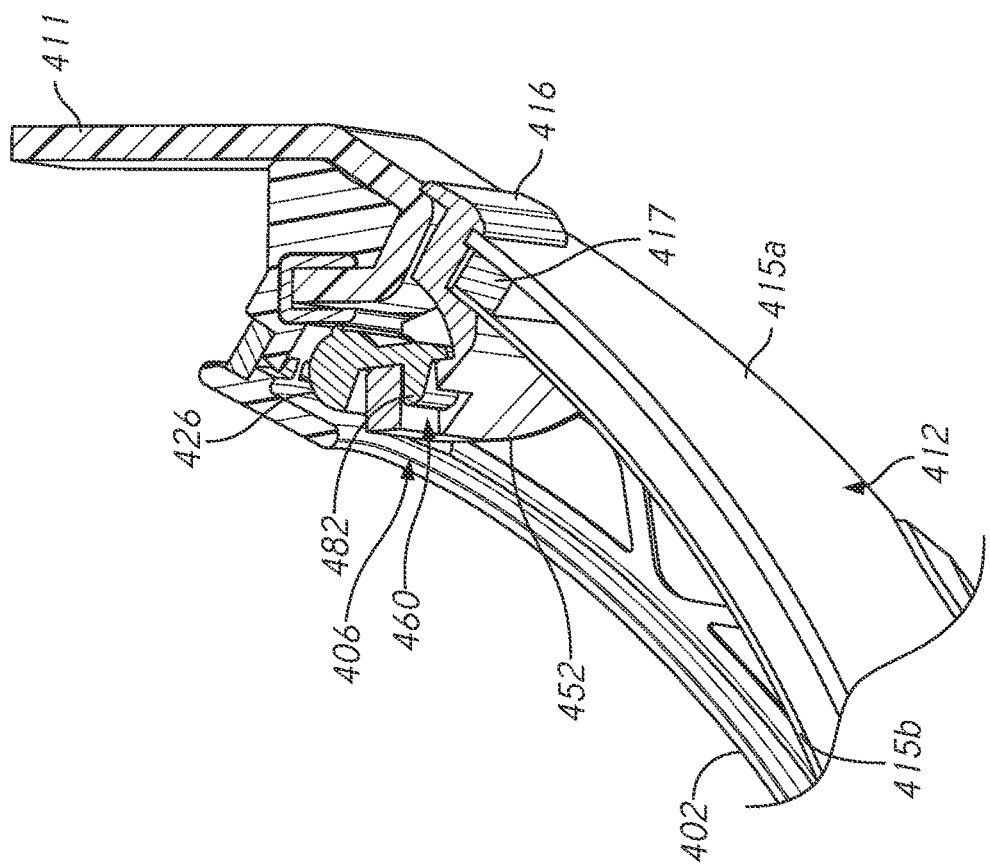

In some embodiments, the magnetic elements 166 are inserted into pockets 164 defined in the face gasket 104 along front surface 173. In some examples, the pockets 164 may have a generally trapezoidal shape oriented such that the openings of the pockets 164 at the front surface 173 are smaller than the bottoms of the pockets 164. The shape of the magnetic elements 166 may generally be trapezoidal shaped to correspond to the shape of the pockets 164 such that the magnetic elements 166 are retained in the pockets 164 with at least a portion of a surface of the magnetic elements 166 exposed along the front surface 173. In other embodiments, the pockets and magnetic elements may have different suitable cooperating shapes, such as begin substantially rectangular prisms or other regular or irregular shapes. In some embodiments, the magnetic elements 166 may be molded in place with the face gasket 104. That is, the magnetic elements 166 may be placed in a mold (e.g. a mold suitable for injection molding) for forming the face gasket 104, and the elastomeric material (e.g., TPU), may be injected into the mold such that it at least partially surrounds the magnetic elements 166 and forms pockets 164. In some embodiments, the magnetic elements 166 are inserted into the pockets 164 after the face gasket 104 is formed. For example, the face gasket 104 may be temporarily deformed (e.g., bent) such that the opening to the pockets 164 are widened. The magnetic elements 166 may be placed inside the pockets 164 during deformation and once the face gasket 104 is returned to its original shape, the magnetic elements 166 may be retained within the pockets 164. In some embodiments, for example as shown in FIG. 11, the pockets 164 may be provided in respective stiffened portions 172 of the face gasket 104. The portions 172 may be formed by the same material (e.g., TPU or other elastomer) as the rest of the face gasket but may be thicker and/or otherwise stiffened to reduce deformation of the face gasket at the locations of pockets 164, for example as compared to other regions along the lens interacting portion 177 or the web 181 of the face gasket 104, which may reduce the risk of the magnetic elements 166 being dislodged from the pockets 164. In some embodiments, the magnetic elements 166 may additionally be bonded (e.g., adhered) to the pockets 164. In some examples, other features may additionally or alternatively be used to reduce the risk of accidental decoupling of a magnetic element from its pocket. Referring to the example in FIG. 23, which shows a partial view of the goggle frame 102, isolation features (e.g., slits 183) may be formed in one or more portions of the face gasket surrounding one or more of the pockets 164, for example one or more of the pockets 164 along the lower portion of the face gasket 104. As shown in FIG. 23, a first pair 185-1 of spaced apart slits 183 may be associated with a pocket 164. Each slit 183 of the pair 185-1 may be formed in a first portion of the face gasket, here just above the pocket 164. Each of the slits 183 of the pair 185-1 may be located on an opposite side of the pocket 164 such that if the face gasket 104 is deformed in a first direction (e.g., bending of the face gasket toward the rear or user-facing side), deformation at the pocket 164 may be reduced by virtue of the modification of the load path caused by the slits 183. In some embodiments, a second pair 185-2 may be formed in a different portion of the face gasket, e.g., on a portion just below the pocket 164, such that deformation at the pocket 164 due to deformation of the face gasket in another direction (e.g., bending the face gasket generally upward) may be reduced.

Referring to FIG. 8, the lens frame 116 may include magnetic materials for magnetic coupling with corresponding magnetic materials on the face gasket 104. For example, the lens frame 116 may include magnetic elements 140 on the rear side 135 of the lens frame 116 on surface 141. The magnetic elements 140 may be recessed into surface 141 and exposed to the rear side 135 (e.g., flush with or below the surface 141) or they may be embedded just below surface 141 such that they are still capable of exerting sufficient magnetic force to attract the magnetic elements on the goggle frame 102. The magnetic elements 140 may be arranged at corresponding locations to the magnetic elements 166 of the face gasket 104, and may include opposing polarities to the magnetic elements 166 such that the magnetic elements 140, 166 are attracted to each other. The magnetic elements 140 may include an exposed surface that is substantially flush with the surface 141. In some examples, surface 141 may be angled at a corresponding angle to an angle of front surface 173 of the face gasket 104 to facilitate alignment of the lens assembly 112 with the goggle frame 102.

As illustrated in FIG. 8, the magnetic elements 140 may be received in pockets 138 defined in the lens frame 116. In some examples, the pockets 138 may have a generally trapezoidal shape oriented such that the openings of the pockets 138 at the surface 141 are smaller than the bottoms of the pockets 138. The shape of the magnetic elements 140 may generally be trapezoidal shaped to correspond to the shape of the pockets 138 such that the magnetic elements 140 are retained in the pockets 138 with at least a portion of a surface of the magnetic elements 140 exposed along the rear side 135. In some embodiments, the magnetic elements 140 may be molded in place with the lens frame 116 in a similar manner as described for magnetic elements 166 in face gasket 104. In some embodiments, the magnetic elements 140 are inserted into the pockets 138 after the lens frame 116 is formed in a similar manner to magnetic elements 166 in face gasket 104. In some embodiments, an adhesive may be applied inside the pockets 138 to provide additional retention of the magnetic elements 140 in the pockets 138.

Positioning and/or alignment of the lens assembly 112 relative to the goggle frame 102 may be achieved at least in part by the shape and/or contours of the corresponding contact surfaces of the lens assembly 112 and the goggle frame 102, which in the illustrated embodiment is defined in part by the shape and wall contours of the peripheral rims of the lens assembly 112 and the goggle frame 102. Additionally or alternatively, positioning and/or alignment of the lens assembly 112 with respect to the goggle frame 102 may be aided by the automatic centering of the magnetic interaction between the lens assembly 112 and the goggle frame 102. In some embodiments, the lens assembly 112 and the goggle frame 102 may include corresponding alignment features to facilitate alignment of the lens assembly 112 to the goggle frame 102. For example, as illustrated in FIGS. 8 and 10, the lens frame 116 and the face gasket 104 may include corresponding extensions or protrusions and recesses or grooves to facilitate alignment of the lens assembly 112 and the goggle frame 102. That is, the extensions and recesses of the lens frame 116 may be configured to mate with corresponding recesses and extensions of the face gasket 104.

Referring to FIG. 10, the face gasket 104 may include one or more goggle frame alignment features such as one or more alignment recesses 168 and/or one or more alignment protrusions 170. The goggle frame alignment features may be provided at suitable locations on the face gasket 104 such as around the perimeter of the face gasket 104. The alignment features (e.g., recesses 168 and protrusion 170) may be arranged among the upper magnetic elements 166 and/or to the lower magnetic elements 166. Referring to FIG. 8, the lens frame 116 may include corresponding lens frame alignment features (e.g., one or more protrusions 142 and/or one or more recesses 144), which may be provided on the rear side of the lens frame, such as on the surface 141. The locations of the alignment features on the lens frame 116 may correspond to the locations of the alignment features on the face gasket 104. An alignment extension may be configured (e.g., sized and shaped) to be received in the alignment recesses which may facilitate alignment of the lens assembly to the goggle frame. The cooperating fit between the goggle frame and lens frame alignment features may also prevent relative sliding movement between the lens assembly 112 and goggle frame 102, such as preventing any substantial up-down movement of the lens assembly 112 relative to the goggle frame 102 in the examples illustrated in FIGS. 8 and 10. In some embodiments, the locations of the protrusions and recesses may be switched between the lens frame 116 and the face gasket 104, or the respective one of the lens frame 116 and face gasket 104 may instead be provided only with recesses or protrusions. In some embodiments, one or more of the alignment features on either the lens frame or face gasket may be a combination of a protrusion and a recess and the corresponding alignment features on the lens frame or face gasket may also be a combination of a protrusion and recess configured for a cooperating fit with its corresponding alignment feature. For example, as illustrated in FIG. 8, some of the lens frame alignment features, such as the upper alignment features, may be a combination of a protrusion 142 and a recess 144, which in this example is located just below the protrusion 142. As shown in FIG. 10, corresponding ones of the goggle frame alignment features, here the upper alignment features, may be a combination of a recess 168 and a protrusion 170, in this case located just below the recess 168, such that the upper protrusions 170 on the face gasket 104 are received in the upper recesses 144 of the lens assembly 116 when the upper protrusions 142 of the lens assembly 116 mate (e.g., are received in) the upper recesses 168 of the face gasket 104.

Magnetic force acting between magnetic materials positioned on opposing faces of the lens assembly 112 and the goggle frame 102 may resist separation of the lens assembly 112 and goggle frame 102. In some examples, the lens assembly 112 may additionally or alternatively be mechanically coupled to the goggle frame 102. For example, the goggle 100 may include one or more latch mechanisms for mechanically interlocking the lens assembly 112 to the goggle frame 102. In some examples, the latch mechanisms may include interlocking latch components located on the lens assembly 112 and goggle frame 102 to resist separation of the lens assembly 112 and the goggle frame 102. In some examples, the latch components may further include magnetic materials that may be configured to magnetically couple the latch components. In some examples, the latch components may mechanically and magnetically engage with each other to secure the lens assembly 112 to the goggle frame 102. The combination of mechanical and magnetic coupling of the latch components may further secure the latch mechanism (e.g., resist inadvertent decoupling of the latch components).

Referring to FIG. 4, the goggle 100 may include one or more latch mechanisms 206 to secure the lens assembly 112 to goggle frame 102. For example, as illustrated in FIG. 4, the goggle 100 may include first and second latch mechanisms 206 at end portions 200-1, 200-2. The latch mechanisms 206 may comprise latch components included with the lens assembly 112 and the goggle frame 102. For example, a first latch component 152 may be included with the lens assembly 112 and a second latch component 180 may be included with the goggle frame 102. As illustrated in FIGS. 1-3, the latch mechanisms 206 may be at least partially concealed by the outriggers 106 and/or face gasket 104 when the lens assembly 112 is coupled to the goggle frame 102.

In some embodiments, the first latch component of a latch mechanism may be included with the lens frame 116. As shown in FIG. 6, a first latch component 152 may protrude from a side portion 132. In the example illustrated in FIG. 6, the first latch component 152 may comprise a tab 154. The tab 154 may include a keyway 160. In some embodiments, the keyway 160 may pass through tab 154, as shown in FIG. 6, or keyway 160 may form an indent in the outer surface of tab 154. In some embodiments, tab 154 may include a seat 157 configured to accept a first magnetic latch element 158. As shown in FIG. 6, the seat 157 may be located at a distal end of the tab 154. In some embodiments, the seat 157 may have a generally trapezoidal shape oriented such that the opening of the seat 157 is smaller than the bottoms of the seat 157. The shape of the first magnetic latch element 158 may generally be trapezoidal shaped to correspond to the shape of the seat 157 such that the first magnetic latch element 158 is retained in the seat 157 with at least a portion of a surface of the first magnetic latch element 158 exposed along a surface of tab 154. In some embodiments, the first magnetic latch element 158 may be molded in place with the lens frame 116 in a similar manner as described for magnetic elements 140 in the lens frame 116. In some embodiments, the first magnetic latch element 158 is inserted into the seat 157 after the lens frame 116 is formed in a similar manner to magnetic elements 140 in lens frame 116. In some embodiments, an adhesive may be applied inside the seat 157 to provide additional retention of the first magnetic latch element 158 in the seat 157.

Tab 154 may include a stop 156 adjacent to the keyway 160 and/or between the keyway and the seat 157. The stop 156 may protrude from the outer surface of tab 154. As can be seen in FIGS. 7 and 12, in some embodiments, the stop 156 may protrude at an angle, forming a substantially wedge-shaped structure. Still referring to FIGS. 7 and 12, the tab 154 may extend from the lens frame 116 at a non-perpendicular angle that more closely follows the general arcuate shape of the lens frame 116. Angling the tab 154 to more closely follow the arc of the lens frame 116 may reduce the risk of the tab 154 getting caught on other components and/or removed from the lens frame 116. The elements of the first latch component 152 of the lens frame 116 may be configured to engage with one or more elements of a second latch component 180 of the goggle frame 102.

As shown in FIG. 14, the second latch component 180 may be included with a rod 126 having a bottom end 125 and a top end 127. The rod 126 may include a key 182 that protrudes from an outer surface of the rod 126 between the bottom end 125 and top end 127. As can be seen in FIG. 12, the key 182 may extend from the rod 126 with a substantially crook-like shape in some examples. The key 182 may be configured to engage the keyway 160 of tab 154. The rod 126 may include a cavity 184 adjacent to the key 182, the cavity 184 configured to accept a second magnetic latch element 186. The cavity 184 may extend through the rod 126, as shown in the example in FIG. 14. The cavity 184 may have a generally trapezoidal shape such that an opening of the cavity 184 adjacent to the key 182 is smaller than an opening of the cavity 184 on a side of the rod 126 opposite the key 182. The second magnetic latch element 186 may have a generally trapezoidal shape that may correspond to the trapezoidal shape off the cavity 184. In some embodiments, the second magnetic latch element 186 may be inserted into the cavity 184 from the side of the rod 126 opposite the key 182 such that at least a portion of a surface of the second magnetic latch element 186 is exposed at the opening of the cavity 184 adjacent to the key 182. In some embodiments, a tab may be included along a periphery of an opening of the cavity 184 on a side of the rod opposite the key 182. The tab may be temporarily deformed as the second magnetic latch element 186 is inserted into the cavity 184. After the second magnetic latch element 186 has been inserted into the cavity 184, the tab may retain the second magnetic latch element 186 in the cavity 184. In other words, in some embodiments, the second magnetic latch element 186 may be snap-fit into the cavity 184. In some embodiments, an adhesive may be used to provide retention or additional retention of the second magnetic latch element 158 in cavity 184. The second magnetic latch element 186 may have a polarity opposite the polarity of the first magnetic latch element 158. The position of cavity 184 and second magnetic latch element 186 may correspond to the location of the seat 157 and first magnetic latch element 158.

The rod 126 may be coupled to an actuator 108 at the bottom end 125. As shown in FIG. 15, the actuator 108 may include a post 190 with one or more prongs 192. The post 190 may be configured to engage an interior of the rod 126 and the one or more prongs 192 may engage prong holes 194 (shown in FIG. 14) in the rod 126 to fixedly attach the actuator 108 to the rod 126. The actuator 108 may be used to rotate the rod 126 about an axis along a length of the rod 126. In some embodiments, the actuator 108 may include a grip feature 109. In the example shown in FIG. 14, the grip feature 109 includes a depression. In other embodiments, the grip feature 109 may include a raised pattern and/or a non-slip coating. The grip feature 109 may facilitate the user actuating the actuator 108.

Figure 13B:
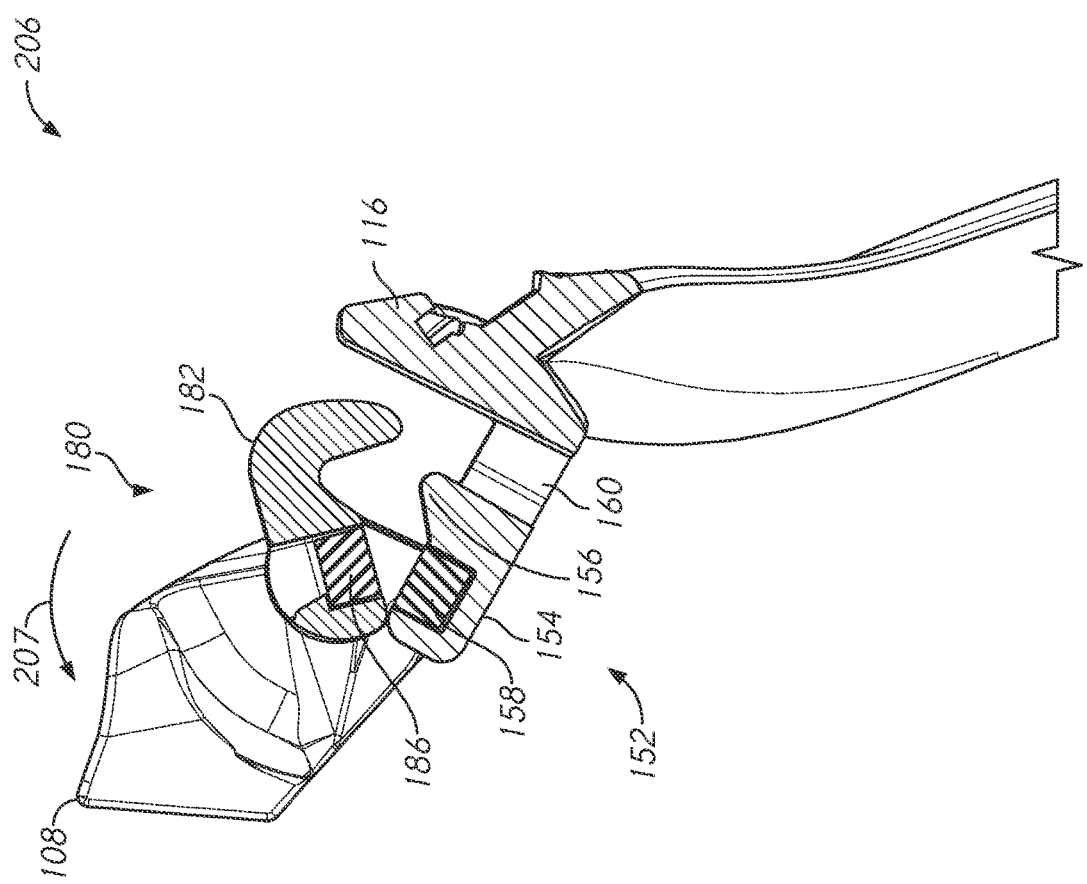
FIG. 13B is a view of a latch mechanism in a disengaged position in accordance with some examples of the present disclosure.

FIGS. 13A and 13B are horizontal sectional views of the latch mechanism 206. FIG. 13A shows the first latch component 152 and the second latch component 180 of the latch mechanism 206 in an engaged position (e.g., latched position) to secure the lens assembly 112 to the goggle frame 102. In the engaged position, at least a portion of key 182 is surrounded by keyway 160. At least another portion of the key 182 abuts stop 156. The stop 156 may restrict the pivotal rotation of the rod 126 when the first latch component 152 and second latch component 180 are engaged. Although key 182 is shown having a substantially crook-shape and stop 156 is shown having a wedge-shape, it is understood that key 182 and stop 156 may take other suitable complementary shapes that allow key 182 to engage keyway 160 (e.g., key 182 may be substantially arc-shaped and stop 156 may be a half-cylinder). Still referring to FIG. 13A, at least a portion of a surface of first magnetic latch element 158 may be adjacent to at least a portion of a surface of the second magnetic latch element 186 in the engaged position. The magnetic latch elements 152, 186 may be coupled by magnetic force. The mechanical engagement of the key 182 with keyway 160 and the magnetic coupling between magnetic latch elements 152, 186 may secure the latch mechanism 206 in the engaged position.

FIG. 13B shows the first latch component 152 and the second latch component 180 of the latch mechanism 206 in a disengaged position (e.g., unlatched position). A user may pivotally rotate rod 126 about an axis along the length of rod 126 to disengage the latch mechanism 206. The user may rotate rod 126 by actuating the actuator 108 as indicated by arrow 207. Pivoting rod 126 may cause key 182 to disengage from keyway 160 and decouple the magnetic attraction between magnetic latch elements 152, 186.

Once the latch mechanism 206 is in the disengaged position, a user may move (e.g., translate) the lens assembly 112 laterally from the goggle frame 102 to remove the lens assembly 112. The lateral movement may decouple the magnetic elements 140 from magnetic elements 166 and disengage alignment extensions 142, 170 from alignment recesses 144, 168. To reattach the lens assembly 112 (or attach a new lens assembly 112), the user may move the lens assembly 112 laterally to couple magnetic elements 140, 166 and engage alignment extensions 142, 170 with alignment recesses 144, 168. The user may then rotate the actuator 108 in a direction opposite arrow 207 to move the latch mechanism 206 into an engaged position to secure the lens assembly 112 to the goggle frame 102.

Figure 16:
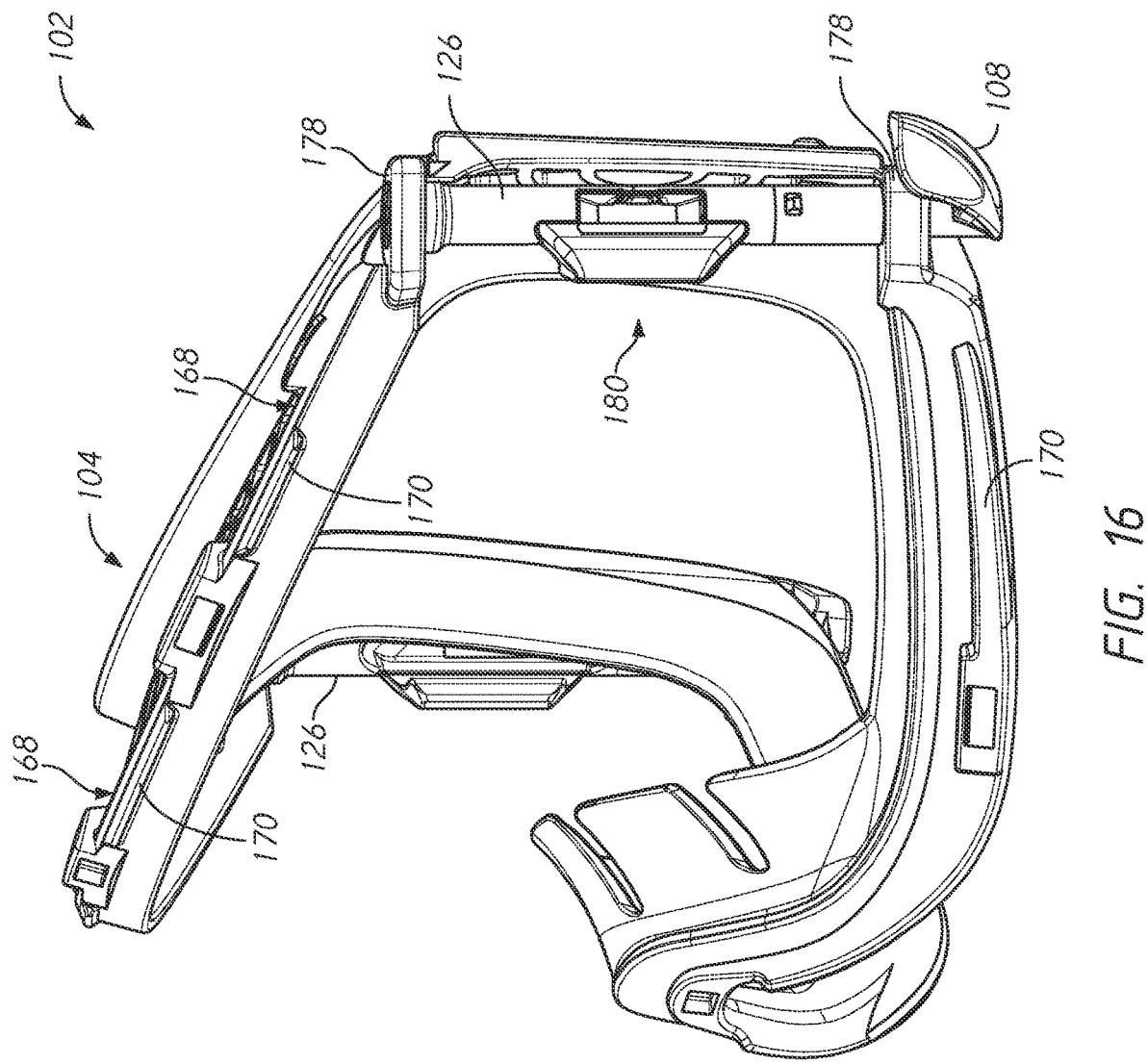
FIG. 16 is a view of a face gasket and latch component in accordance with some examples of the present disclosure.
Figure 17:
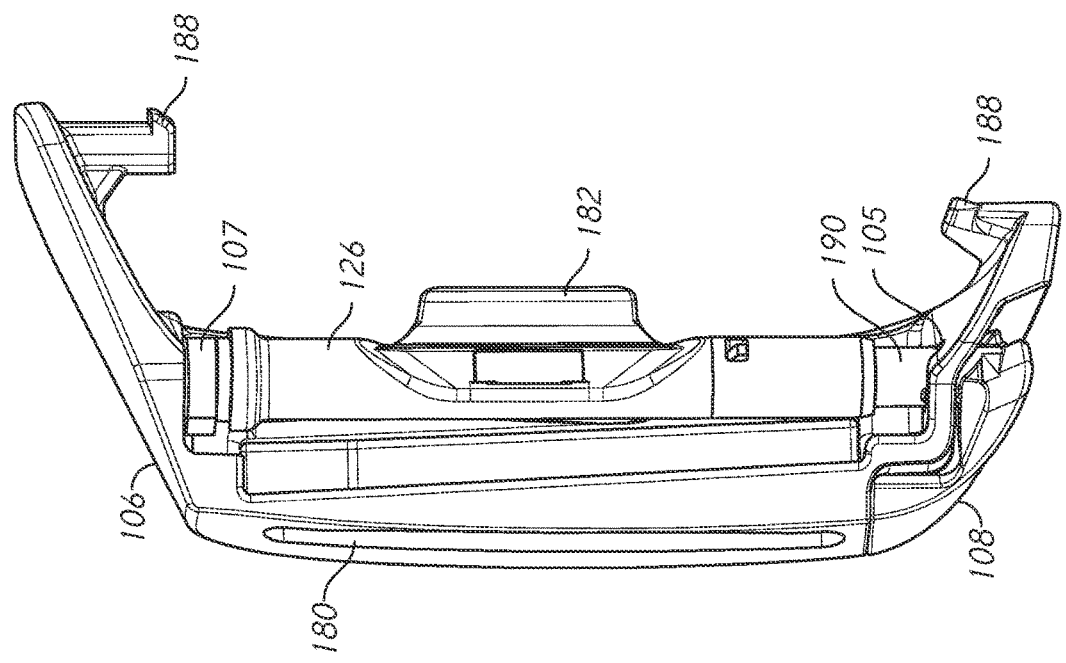
FIG. 17 is a view of an outrigger and latch component in accordance with some examples of the present disclosure.

To facilitate the rotation of the second latch component 180 by the actuator 108, the rod 126 may be pivotally coupled to the goggle frame 102. In some embodiments, the rod 126 may be pivotally coupled to the face gasket 104 and outrigger 106. As shown in FIGS. 11 and 16, face gasket 104 may include rod accepting holes 178 at top portion 202 and bottom portion 204 of goggle 100. As shown in FIG. 17, outrigger 106 may include opening 105 at the bottom portion 204 of goggle 100 and a socket 107 at the top portion 202 of goggle 100. As shown in FIG. 16, portions of ends 125, 127 of the rod 126 may pass through the rod accepting holes 178 of the face gasket 104. As shown in FIG. 17, the top end 127 of the rod 126 may be pivotally accepted in socket 107 of outrigger 106. Referring to FIGS. 3, 16, and 17, post 190 of the actuator 108 may pass through the opening 105 of the outrigger 106 and rod accepting hole 178 in bottom portion 204 to engage the interior of rod 126. At least a portion of the actuator 108 may be exposed by the outrigger 106. Rod 126 may be pivoted within the face gasket 104 and outrigger 106.

Figure 21A:
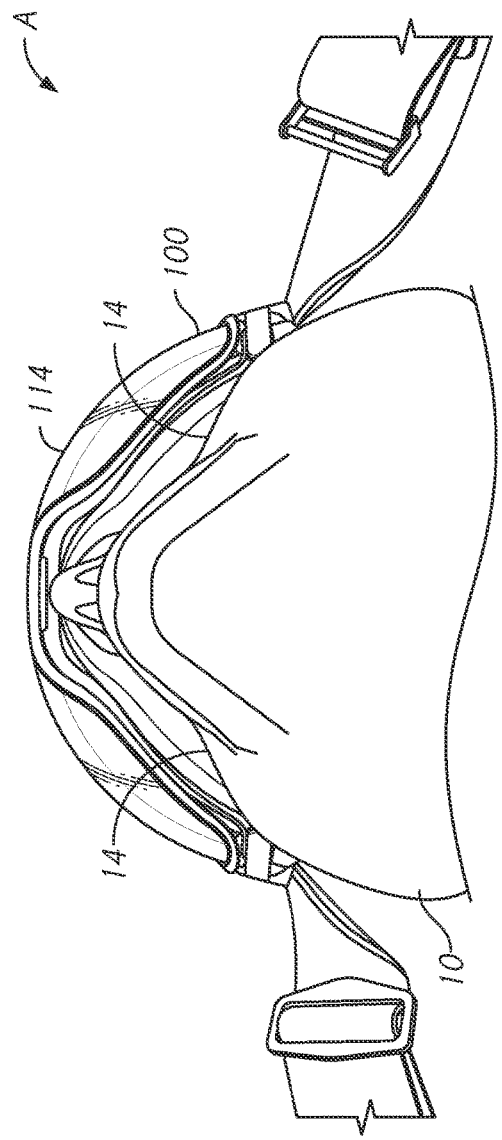
FIG. 21A shows a bottom view of a goggle according to the present invention against a user's face.
Figure 21B:
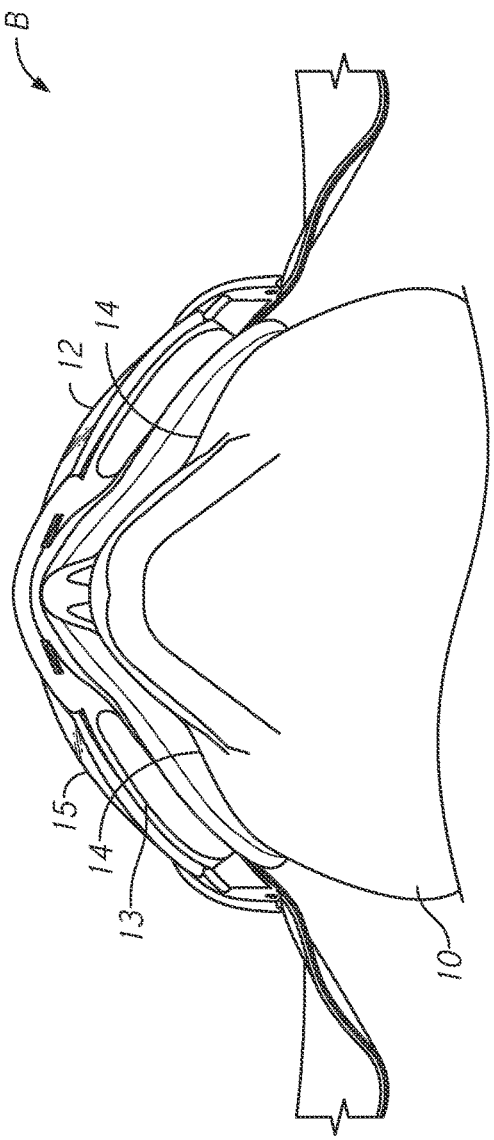
FIG. 21B shows a bottom view of a conventional goggle against a user's face.

FIGS. 21A and 21B show a "side by side" comparison of an enlarged downward field of view of a goggle having a goggle lens with compound curvature according to the present disclosure (e.g., goggle 100), shown in FIG. 21A, and the more limited (or smaller) downward field of a conventional goggle 12, shown in FIG. 21B. As seen in FIG. 21A, the shape of the goggle lens(es) of goggle 100, in combination with the unique cooperating shape of the frame, allows the lens(es) to be brought closer to the user's cheeks 14, providing additional unobstructed region in the downward viewing direction as compared to that of a conventional goggle 12, in which the lower part of the goggle frame 13 must extend farther out from the user's face (e.g., form the cheeks 14) to meet the lens 15, thereby obstructing most of the downward viewing direction.

FIGS. 22A and 22B, show another "side by side" illustration of the enlarged downward field of view of a goggle (e.g., goggle 100) having a compound curvature goggle lens according to the present disclosure as compared to a more limited downward field of view of an existing goggle 22. The views in FIGS. 22A and 22B are longitudinal section views, looking down (as indicated by line 22A-22A in FIG. 2) of the respective goggle. As shown in FIG. 22B, the face gasket of a goggle, such as goggle 22, typically has a user-facing side and the lens facing sides connected by webbing, which in conventional goggles, such as goggle 22 extends along most of the upper and most of the lower portion of the goggle, excepting the nose region, to position the lens in a location spaced from the user's face. Like existing goggles, goggle 100 has a similar configuration along the upper portion of the face gasket. However, unlike existing goggles, the goggle 100 may lack substantially any webbing or have significantly narrower webbing, as indicated by D along the lower portion of the goggle frame, which cooperates with the unique shape of lens 114 to bring the lens 114 closer to the user's face at the lower portion of the goggle, enhancing the downward field of view of the goggle 100. In contrast, the existing goggle 22 has a wider webbing in the lower portion of the frame 23, as indicated by $D_C$, thereby resulting in a larger amount of the downward field of view being obstructed by the frame 23.

While lens assembly and more specifically the lens (e.g., inner and outer lenses 114 and 116, respectively) are described with reference to a goggle designed for quick interchange, it will be understood that the features and benefits provided by the compoundly curved lenses herein may be used with a goggle having a fixed (i.e., non-removably) coupled lens. Therefore, aspects of the present disclosure associated with removably coupling a lens assembly to a goggle frame may be optional and in some embodiments, the lens, or inner and outer lenses in the case of a dual-lens design, may be fixed to the goggle frame and not intended for removal by the user. In yet other examples, a goggle lens with a compound curvature as described herein may be removably coupled to the goggle frame using any suitable conventional techniques such as by inserting and retaining the lens directly to the goggle frame (e.g., via tabs or other lens features configured to cooperate directly with retention features of the goggle frame). In some such examples, a compoundly curved lens, or dual-lens assembly in which at least one lens has a compound curvature as described herein, may be coupled to the goggle frame without utilizing a lens frame.

FIGS. 24, 25, and 26A-B, illustrate views of a goggle in accordance with further examples of the present disclosure. Like goggles in other examples herein, the goggle 400 may include a lens assembly 412, which is removably coupled to a goggle frame 402 to facilitate quick and easy (e.g., in the field and without use of any additional tools) lens interchange. To that end the lens assembly 412 and goggle frame 402 may be provided with one or multiple types of attachment mechanisms or features for removable retaining the lens assembly 412 on the goggle frame 402. The goggle 400 may include a first type of (e.g., magnetic) attachment or retention mechanism and a second type of attachment or retention mechanism, at least a part of which may rely on mechanical interference for retaining the lens, which may reduce the risk of inadvertent (i.e., unintentional) separation of the lens from the goggle. In some examples, the second type of retention mechanism may be a latch, which may optionally and additionally include magnetic retention as part of the mechanical latching effected by the latch. The latch mechanism 406 of the goggle 400 may similarly include an actuator 408 for engaging and disengaging the latch.

The lens assembly 412 may include at least one unitary lens 415, which is coupled to and thus supported by a lens frame or bracket 416. Like the lens frame 116, the lens frame 416 may be configured for quick lens interchange. The lens frame 416 may be configured to be attached to and detached from the goggle frame any number of times (e.g., hundreds, thousands) as may be desired by a user. The lens frame 416 may thus include some or all of the features of the lens frame 116. For example, the lens frame 416 may include a plurality of magnetic elements The lens assembly 412 may be a dual-lens assembly including an outer lens 415a and an inner lens 415b. The outer lens 415a and an inner lens 415b may be spaced apart ant attached to one another via a lens spacer 417 (e.g., a foam adhesive) forming a dual-lens structure 401. The dual-lens structure 401 may be coupled to the lens frame 416 via any suitable means. In some examples, the dual-lens structure 401 may be fixedly coupled to the lens frame 416, which implies that the dual-lens structure 401 is not intended to be removed from the lens frame 416 by the user during normal use of the goggle 400. For example, the dual-lens structure 401 may be adhered by a surface adhesive applied between the dual-lens structure 401 and the lens frame 416 or otherwise bonded thereto. In other embodiment, the dual-lens structure 401 may be removably coupled such that the user may be able to replace or exchange one dual-lens structure 401 with another.

In the present example, the dual-lens structure 401 is coupled to the lens frame 416 via mechanical interlocking of the tabs 462 extending from lateral ends of the outer lens 415*a* and the slots 434 formed in the lateral portions of the lens frame 416. Alternatively or additionally, the dual-lens structure 401 may include interlocking features at other peripheral locations, for example along the upper and/or lower edges of one or both of the lenses 415. As shown in FIG. 26, at least one of the lenses 415 may be provided with tabs along the upper and/or lower edges of the lens 415, which may be received in corresponding recesses or slots in the upper portion 428 and/or the lower portion 430 of the lens frame 416. To provide a substantially rimless design, only a portion of the lens frame 416, such as the upper portion 428 and/or lower portion 430, or suitable segments thereof, may protrude in front of the outer lens 415*a*. As described, the dual-lens structure 401 may be removably coupled to the lens frame 416, or it may be fixed to the lens frame 416, for example by bonding the rear (user-facing) side of the lens 415 (e.g., inner lens 415*b*) to the forward-facing surface of the lens frame 416.

In this example, the strap 411 is coupled (e.g., adhered via an adhesive 437, mechanically fastened and/or otherwise suitably attached) directly to the goggle frame 402, such as by being received and adhered into the slot 431. The face gasket 404 may include a strap support, which may be provided by a separate component, permanently fixed to the face gasket or by a stiffened portion (e.g., by an increase in thickness and/or use of a stiffer material than the remainder) of the face gasket, which may reduce deformation of the face gasket responsive to forces applied by the strap.

The goggle 400 may include alignment features, which may facilitate the alignment of the lens assembly 412 to the goggle frame 404. In some embodiments such as the present embodiment, the alignment features may be integrated with the pockets that house the magnetic elements, also referred to as magnet housings. For example, the magnetic elements 440 of the lens assembly 412 may be provided in individual pockets 438 that protrude from the rear (user-facing) side of the lens assembly 412. The magnetic elements 466 of the goggle frame 402 may be provided in pockets 464, the forward-most faces of which are recessed from the lens-facing side of the goggle 400. As such, the cooperating fit between the protruding pockets 438 and the recessed pockets 464 may facilitate alignment and/or prevent lateral movement of the lens assembly 412 relative to goggle frame 404.

Similar to goggle 100, the goggle 400 may include a latch mechanism 406 at each of the lateral ends of the goggle 100 for more securely coupling the lens assembly 412 to the goggle frame 402. The latch mechanism 406 may include some or all of the features of latch mechanism 206. For example, the latch mechanism 406 may include a first latch component 452, e.g., a tab 454 with a keyway 460, on the lens assembly 412, which is configured to couple to a second latch component 480, e.g., a pivoting rod 426 with a key 482 protruding from the rod 426 and configured to operatively engage the keyway 460 to latch the lens assembly 412 to the goggle frame 402. The latch mechanism 406 may but need not include magnetic elements. The operation of the latch mechanism 406 may be similar to that of the latch mechanism of goggle 100, which for conciseness will not be repeated.

Inventive combinations according to further examples of the present disclosure are provided in the following enumerated paragraphs. It is further noted that inventive embodiments may include combinations of features in different groups of enumerated paragraphs, for example the features of a goggle in accordance with any of the paragraphs in groups A, B, C, or D may be combined with features in a different enumerated group A, B, C, or D.

A1. A goggle comprising:
a lens assembly comprising:
an outer lens having a first surface and a second surface opposite the first surface;
an elastomer lens frame coupled to the outer lens along a portion of a perimeter of the second surface, wherein the lens frame comprises a plurality of first magnet pockets;
a corresponding plurality of first magnetic elements, each received in a respective one of the first magnet pockets; and
a first latch component coupled to the lens frame; and a goggle frame comprising:
an elastomer face gasket configured for removably coupling to the lens assembly thereto, wherein the elastomer face gasket comprises a plurality of second magnet pockets arranged along a perimeter of the face gasket; and
a corresponding plurality of second magnetic elements, each received in a corresponding one of the second magnet pockets, wherein the second magnet pockets and magnetic elements are arranged along the perimeter of the face gasket to align with and magnetically attach to the plurality of first magnetic elements; and
a second latch component a configured to engage the first latch component to mechanically secure the lens frame to the goggle frame.

A2. The goggle of paragraph A1, wherein the face gasket comprises a plurality of thick portions arranged along the perimeter of the face gasket, wherein the plurality of first magnet pockets are included in the plurality of thick portions.

A3. The goggle of paragraph A1 or A2, wherein the face gasket is relatively stiffer at the plurality of thick portions along the perimeter than at other locations along the perimeter.

A4. The goggle of any of paragraphs A1-A3, wherein the face gasket comprises at least one of a recess or an extension and the lens frame comprises a corresponding extension or recess, wherein the corresponding extension or recess of the lens frame is configured to mate with the at least one recess or extension of the face gasket.

A5. The goggle of any of paragraphs A1-A4, wherein the goggle frame further comprises an outrigger fixedly coupled to a periphery of the face gasket.

A6. The goggle of any of paragraphs A1-A3, wherein the first latch component includes a first magnetic latch element and the second latch component includes a second magnetic latch element, wherein the first magnetic latch element and the second magnetic latch element are configured to magnetically couple when the first latch component and the second latch component are mechanically engaged.

A7. The goggle of any of paragraphs A1-A3, wherein the first latch component comprises a tab including a keyway and the second latch component comprises a rod pivotally coupled to a periphery of the face gasket, wherein the rod includes a key configured to engage the keyway.

B1. A goggle comprising:
a lens assembly comprising:
an outer lens having a first surface and a second surface opposite the first surface;
a lens frame having a front facing side adjacent to the second surface of the outer lens and fixed to the second surface along only a portion of a perimeter of the second surface; and
a plurality of first magnetic elements arranged along a perimeter of the lens frame on a rear facing side of the lens frame; and
a goggle frame comprising:
a face gasket configured for removably coupling to the lens assembly thereto;
a plurality of second magnet magnetic elements arranged along a perimeter of the face gasket to align with and magnetically attach to the plurality of first magnetic elements; and
a first latch component configured to mechanically secure the lens frame to the face gasket.

B2. The goggle of paragraph B1, wherein the outer lens further comprises a tab extending from a periphery of the outer lens and the lens frame comprises a slot at a periphery of the lens frame, the slot configured to engage the tab to couple the outer lens to the lens frame.

B3. The goggle of paragraph B2, wherein an upper portion of the perimeter and a lower portion of the perimeter of the outer lens are coupled to the lens frame by an adhesive and the tab is on a side portion of the periphery.

B4. The goggle of any of paragraphs B1-B3, wherein the lens frame includes a channel in a periphery of the lens frame, the channel defined by a first ridge and a second ridge, wherein a surface of the outer lens contacts the first ridge and the second ridge when the outer lens is coupled to the lens frame.

B5. The goggle of paragraph B4, wherein the first ridge has a first vent hole proximate a first end of the channel and the second ridge has a second vent hole proximate a second end of the channel, wherein the first and second vent holes permit airflow between the inner lens and the outer lens.

B6. The goggle of any of paragraphs B1-B5, wherein the lens frame further includes a second latch component configured to mechanically engage the first latch component, the first latch component including a first magnetic latch element and the second latch component including a second magnetic latch element, wherein the first magnetic latch element and the second magnetic latch element are configured to magnetically couple when the first latch component and the second latch component are mechanically engaged.

B7. The goggle of paragraph B6, wherein the first latch component further comprises a rod pivotally coupled to a periphery of the face gasket, wherein the rod includes a key, and the second latch component comprises a tab including a keyway configured to engage the key.

C1. A goggle comprising:
a lens assembly comprising:
  an outer lens;
  a lens frame coupled to a rear surface of the outer lens;
  a plurality of first magnetic elements arranged along a perimeter of the lens frame and facing away from the rear surface of the outer lens; and
  a first latch component coupled to the lens frame; and
a goggle frame comprising:
  a face gasket;
  a plurality of second magnetic elements coupled to the face gasket along a periphery of the goggle frame; and
  a second latch component coupled to the face gasket, wherein the second latch component is configured to mechanically and magnetically engage the first latch component for mechanically securing the lens assembly to the goggle frame.

C2. The goggle of paragraph C1, wherein the face gasket further includes:
  an outrigger coupled to a periphery of the face gasket; and
  the second latch component comprises a rod pivotally coupled to the outrigger, wherein the rod includes a key protruding from a surface of the rod.

C3. The goggle of paragraph C2, wherein the goggle frame further comprises an actuator coupled to a first end of the rod to pivot the rod with respect to the outrigger responsive to a force applied to the actuator.

C4. The goggle of paragraph C3, wherein the actuator comprises a post inserted into an interior of the rod.

C5. The goggle of paragraph C4, wherein the outrigger comprises an opening, wherein the post extends through the opening of the outrigger to engage the interior of the rod, the post rotatable within the opening.

C6. The goggle of paragraph C5, wherein the face gasket comprises a first hole and a second hole, wherein a cylindrical portion of the outrigger extends through the first hole to pivotally engage a second end of the rod and the post extends through the second hole to engage the interior of the rod, wherein the second hole of the face gasket aligns with the opening of the outrigger.

C7. The goggle of any of paragraphs C2-C6, wherein the first latch component comprises a tab extending from a periphery of the lens frame, wherein the tab includes a stop protruding from a surface of the tab and a keyway adjacent to the stop, wherein the keyway extends from the surface of the tab to an interior of the tab, wherein the keyway is configured to engage the key of the rod and the stop is configured to limit pivotal movement of the rod when the lens frame is coupled to the goggle frame.

C8. The goggle of paragraph C7, wherein the rod further comprises a first magnetic latch element and the tab comprises a second magnetic latch element, wherein the first magnetic latch element and the second magnetic latch element are configured to couple via magnetic attraction when the key of the rod and the keyway of the tab are engaged.

C9. The goggle of any of paragraphs C1-C8, wherein the outer lens further comprises a tab extending from a periphery of the outer lens and the lens frame comprises a slot at a periphery of the lens frame, the slot configured to engage the tab to couple the outer lens to the lens frame.

C10. The goggle of paragraph C9, wherein an upper portion of the perimeter and a lower portion of the perimeter of the outer lens are coupled to the lens frame by an adhesive and the tab is on a side portion of the periphery.

C11. The goggle of any of paragraphs C1-C10, wherein the face gasket comprises at least one of a recess or an extension and the lens frame comprises a corresponding extension or recess, wherein the corresponding extension or recess of the lens frame is configured to mate with the at least one recess or extension of the face gasket.

C12. The goggle of any of paragraphs C1-C11, wherein the first plurality of magnetic elements are at least partially embedded in pockets in the face gasket and the face gasket comprises thickened portions surrounding the pockets.

C13. The goggle of any of paragraphs C1-C12, wherein the outer lens has an upper portion having a first radius of curvature and a lower portion having a second radius of curvature, wherein the first radius and second radius are different.

C14. The goggle of paragraph C13, wherein the outer lens has a first end portion and a second end portion, wherein a radius of curvature from the first end portion to the second end portion is constant.

D1. A method of removing a lens assembly from a goggle frame, the method comprising:
actuating an actuator to rotate a rod with respect to the goggle frame, wherein rotating the rod disengages a key of the rod from a keyway of the lens assembly and further disengages a first magnetic latch element of the lens assembly from a second magnetic latch element of the rod; and
after actuating the actuator, laterally translating the lens assembly away from the goggle frame, wherein laterally translating the lens assembly disengages a magnetic coupling between a first plurality of magnetic elements of the goggle frame from a second plurality of magnetic elements of the lens assembly.

E1. A goggle comprising:
a goggle frame; and
a lens assembly coupled to the goggle frame and comprising:
an outer lens having a first surface and a second surface opposite the first surface; and
a elastomeric lens frame coupled to the outer lens along a portion of a perimeter of the second surface.

E2. The goggle of paragraph E1, wherein the outer lens further comprises a tab extending from a periphery of the outer lens and the flexible lens frame comprises a slot at a periphery of the flexible lens frame, the slot configured to engage the tab to couple the outer lens to the flexible lens frame.

E3. The goggle of paragraph E2, wherein the tab is on a side portion of the periphery E4. The goggle of any of paragraphs E1-E3, wherein an upper portion of the periphery and a lower portion of the perimeter of the outer lens are coupled to the flexible lens frame by an adhesive.

E5. The goggle of paragraph E4, wherein the adhesive is a tape adhesive.

E6. The goggle of any of paragraphs E1-E5, wherein the flexible lens frame comprises an elastomer.

E7. The goggle of paragraph E6, wherein the elastomer comprises thermoplastic polyurethane.

F1. A lens assembly for a goggle comprising:
a lens frame;
an outer lens coupled to a front side of the lens frame; and
an inner lens coupled to a rear side of the lens frame to define an interstitial space between the inner and outer lenses;
wherein the lens frame comprises a plurality of vent openings fluidly connecting the interstitial space to an exterior of the lens assembly to allow air to exit from the interstitial space through one of the plurality of openings while air enters the interstitial space through the other one of the plurality of vent openings.

F2. The goggle of paragraph F1, wherein the interstitial space between the inner and outer lenses is sealed to airflow but for air flowing into and out of the interstitial space through the plurality of vent openings.

F3. The goggle of paragraph F1 or F2, wherein the outer lens comprises a first surface and a second opposite the first surface, wherein a least a portion of the lens frame is made from an elastomeric material, and wherein the portion comprises a plurality of ridges extending from the front side of the lens frame, the plurality of ridges pressing against the second surface of the outer lens to seal the interstitial space between the inner and outer lenses from airflow but for airflow enabled via the plurality of vent openings.

F4. The lens assembly of paragraph F3, wherein the plurality of ridges includes a first pair of ridges at one lateral side of the lens frame and a second pair of ridges at an opposite lateral side of the lens frame, each of the first and second pair of ridges comprising a first ridge and second ridges extending along the respective lateral side of the lens frame and spaced laterally apart from one another to define a channel therebetween, and wherein each of the first and second ridges of each of the first and second pairs of ridges includes a vent opening.

F5. The lens assembly of paragraph F4, wherein vent openings in the first and second ridge of a respective pair of ridges are offset from one another in the lateral direction.

It will be further appreciated that although certain advantages or benefits are discussed with reference to some of the embodiments herein, some embodiments of the present disclosure may not provide all or any of these advantages or benefits.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A goggle comprising:
a goggle frame configured to be worn conformally on a user's face, the goggle frame comprising a flexible face gasket that defines an opening configured to encircle the user's eyes when the goggle is worn; and
a lens assembly coupled to the goggle frame and comprising a lens bracket supporting a unitary lens that covers the opening such that an enclosed space is defined between the lens, the goggle frame, and the user's face, when the goggle is worn, wherein the lens has an upper portion having a substantially constant radius of curvature along a vertical direction, a horizontal direction, or both, and wherein the lens has a lower portion having a variable radius of curvature at least along the vertical direction, wherein the upper portion and the lower portion are separated by a first longitudinal line, wherein along a first meridian of the lens perpendicular to the first longitudinal line, the upper portion has a first constant radius of curvature and along the lower portion has a second variable radius of curvature, and wherein along a second meridian of the lens perpendicular to the first longitudinal line, the upper portion has the first constant radius of curvature and along the lower portion has a third variable radius of curvature different than the second variable radius of curvature, and wherein the radius of curvature of the lens varies along a second longitudinal line parallel to the first longitudinal line in the lower portion.

2. The goggle of claim 1, wherein a radius of maximum curvature of the lens is located in the lower portion of the lens.

3. The goggle of claim 2, wherein a lower peripheral edge of the lens is contoured to define a nose recess, wherein the upper portion of the lens extends from an upper peripheral edge of the lens toward the nose recess, and wherein the lower portion of the lens comprises left and right lower portions located on opposite sides of the nose recess.

4. The goggle of claim 3, wherein the lens is adhered to the lens bracket only along the upper peripheral edge and the lower peripheral edge, and wherein the lens is mechanically coupled to the lens bracket along lateral edges of the lens.

5. The goggle of claim 1, wherein the upper portion is either cylindrical or spherical and the lower portion is neither cylindrical nor spherical.

6. The goggle of claim 1, wherein the lens bracket is configured for removably coupling the lens assembly to the goggle frame.

7. The goggle of claim 6, wherein the lens bracket comprises a plurality of magnets for magnetically removably coupling the lens assembly to the goggle frame.

8. The goggle of claim 7, wherein the flexible face gasket comprises a user-facing side and a lens-facing side opposite the user facing side, wherein the lens bracket is coupled to the lens-facing side, and wherein both the user-facing side and the lens-facing side are formed of an elastomer.

9. The goggle of claim 7, wherein the lens bracket is further configured to mechanically couple to the goggle frame.

10. The goggle of claim 9, wherein the goggle frame further comprises an outrigger non-movably coupled to the face gasket.

11. The goggle of claim 10, wherein the lens assembly includes a tab configured for insertion behind the outrigger and a latch operatively associated with the outrigger and configured to engage the tab to mechanically couple the lens bracket to the goggle frame.

12. The goggle of claim 11, wherein the latch comprises an interlocking feature configured to mechanically engage the tab for securing the lens assembly to the goggle frame.

13. The goggle of claim 12, wherein the latch further comprises a magnetic element configured to magnetically engage the tab for securing the lens assembly to the goggle frame.

14. The goggle of claim 12, wherein the latch comprises a rod arranged to pivot about an axis extending substantially vertically and wherein the rod includes a pawl extending radially from the rod and configured to be received within an aperture of the tab for mechanically engaging the tab.

15. The goggle of claim 1, wherein the lens is an outer lens, the lens assembly further comprising an inner lens coupled to the lens bracket such that the inner and outer lenses are spaced apart by the lens bracket to define an interstitial space therebetween.

16. The goggle of claim 15, wherein the inner lens is fixed to the bracket along substantially a full perimeter of the inner lens, and wherein the outer lens is fixed to the lens bracket along only a portion of a perimeter of the outer lens.

17. The goggle of claim 1, wherein the lens has a substantially constant thickness.

18. The goggle of claim 1, wherein a curvature of the lens is greatest proximal to an edge of the goggle away from a nose recess.

19. The goggle of claim 1, wherein the radius of curvature of lens decreases along the first meridian from the first longitudinal line to a bottom of the goggle, and wherein the radius of curvature of the lens decreases along the second longitudinal line from a nose recess to a side of the goggle.

20. The goggle of claim 1, wherein a greatest degree of curvature of the lens is located outside a main field of view of a wearer of the goggle.

21. The goggle of claim 1, wherein a curvature along the first meridian in the lower portion is not definable by a quadratic form.

22. The goggle of claim 1, wherein a curvature of the lower portion of the lens corresponds to a freeform curve.

23. A lens assembly for a goggle, the lens assembly comprising at least one curved lens, having a curvature that varies along a surface of the at least one lens, the at least one lens having an upper portion with a substantially constant radius of curvature along a vertical direction, a horizontal direction, or both, the at least one lens further having a lower portion with a variable radius of curvature along the vertical direction, the horizontal direction, or both, wherein the upper portion and the lower portion are separated by a first longitudinal line, wherein along a first meridian of the lens perpendicular to the first longitudinal line, the upper portion has a first constant radius of curvature and along the lower portion has a second variable radius of curvature, and wherein along a second meridian of the lens perpendicular to the first longitudinal line, the upper portion has the first constant radius of curvature and along the lower portion has a third variable radius of curvature different than the second variable radius of curvature, and wherein the radius of curvature of the lens varies along a second longitudinal line parallel to the first longitudinal line in the lower portion.

24. The lens assembly of claim 23, wherein a radius of maximum curvature of the at least one lens is located in the lower portion.

25. The lens assembly of claim 23, wherein the upper portion is either cylindrical or spherical and the lower portion is neither cylindrical nor spherical.

26. The lens assembly of claim 23, wherein the upper portion extends from an upper peripheral edge of the lens toward a nose region of the goggle, and wherein the lower portion comprises left and right lower portions extending from a bottom edge of the upper portion toward the bottom edge of the goggle on left and right sides, respectively, of the nose region.

27. The lens assembly of claim 23, wherein the at least one lens is a first lens, the lens assembly includes a second lens coupled to the first lens via a lens bracket providing the first and second lens in a spaced relationship to define an interstitial space therebetween.

28. The lens assembly of claim 23, wherein the lens bracket is configured for removably coupling the lens assembly to the goggle.

29. A dual-lens structure comprising a first lens and a second lens attached to the first lens in a spaced-apart arrangement to define an interstitial space between the first and second lenses, wherein at least one lens of the first lens and the second lens comprises a unitary lens made from a monolithic lens body and wherein the at least one lens has an upper portion with a substantially constant radius of curvature along a vertical direction, a horizontal direction, or both, the at least one lens further having a lower portion with a variable radius of curvature along the vertical direction, the horizontal direction, or both, Wherein the upper portion and the lower portion are separated by a first longitudinal line, wherein along a first meridian of the lens perpendicular to the first longitudinal line, the upper portion has a first constant radius of curvature and along the lower portion has a second variable radius of curvature, and wherein along a second meridian of the lens perpendicular to the first longitudinal line, the upper portion has the first constant radius of curvature and along the lower portion has a third variable radius of curvature different than the second variable radius of curvature and wherein the radius of curvature of the lens varies along a second longitudinal line parallel to the first longitudinal line in the lower portion.

30. The dual-lens structure of claim 29, wherein the first lens and the second lens are spaced apart and attached to one another using a lens bracket configured for removably coupling the dual-lens structure to a goggle frame.

\* \* \* \* \*